US 8,419,675 B2

(12) United States Patent
Hayakawa

(10) Patent No.: US 8,419,675 B2
(45) Date of Patent: Apr. 16, 2013

(54) APPLICATOR

(75) Inventor: Koichi Hayakawa, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 131 days.

(21) Appl. No.: 12/869,986

(22) Filed: Aug. 27, 2010

(65) Prior Publication Data

US 2010/0331766 A1      Dec. 30, 2010

Related U.S. Application Data

(63) Continuation of application No. PCT/JP2009/053320, filed on Feb. 25, 2009.

(30) Foreign Application Priority Data

Feb. 29, 2008   (JP) .................................. 2008-050371
Jun. 30, 2008   (JP) .................................. 2008-171828

(51) Int. Cl.
| | |
|---|---|
| *A61M 37/00* | (2006.01) |
| *A61M 1/00* | (2006.01) |
| *A61M 3/00* | (2006.01) |
| *A61M 5/178* | (2006.01) |
| *A61M 5/00* | (2006.01) |
| *A61M 31/00* | (2006.01) |

(52) U.S. Cl.
USPC .................. 604/24; 604/23; 604/26; 604/27; 604/43; 604/45; 604/82; 604/158; 604/164.01; 604/170.03; 604/257; 604/258; 604/275

(58) Field of Classification Search .............. 604/23, 604/24, 26, 27, 39, 40, 43, 45, 68, 69, 70, 604/82, 158, 164.01, 164.09, 164.11, 170.03, 604/191, 257, 258, 275, 36, 164.02, 164.07, 604/166.01, 167.01, 167.06, 276, 278
See application file for complete search history.

(56) References Cited

U.S. PATENT DOCUMENTS

| | | | | | |
|---|---|---|---|---|---|
| 2,148,541 | A | * | 2/1939 | Dierker ........................... | 604/40 |
| 5,364,405 | A | * | 11/1994 | Zaleski ........................... | 606/107 |
| 5,740,965 | A | * | 4/1998 | Miyagi et al. .................. | 239/423 |
| 6,228,051 | B1 | | 5/2001 | Trumbull | |
| 6,540,716 | B1 | | 4/2003 | Holm | |
| 2006/0235450 | A1 | | 10/2006 | Kasahara et al. | |

FOREIGN PATENT DOCUMENTS

| | | |
|---|---|---|
| JP | 5-168714 A | 7/1993 |
| JP | 8-281152 A | 10/1996 |
| JP | 2001-269348 A | 10/2001 |
| JP | 2001-522270 A | 11/2001 |
| JP | 2002-513611 A | 5/2002 |
| JP | 2002-282368 A | 10/2002 |
| JP | 2006-087609 A | 4/2006 |

OTHER PUBLICATIONS

International Search Report (PCT/ISA/210) issued on Apr. 14, 2009, by Japanese Patent Office as the International Searching Authority for International Application No. PCT/JP2009/053320.

* cited by examiner

*Primary Examiner* — Kevin C Sirmons
*Assistant Examiner* — Shefali Patel
(74) *Attorney, Agent, or Firm* — Buchanan Ingersoll & Rooney PC

(57) ABSTRACT

An applicator insertable into a living body includes a nozzle having an elongated nozzle main body and a nozzle head on a front end side of the nozzle main body and through which a liquid together with a gas is expelled, with the nozzle main body including a flexible curved section. The applicator also includes an outer tube in which is positioned a portion of the nozzle main body so as to be movable along a longitudinal direction. The angle or degree of curvature of the curved section is changed by inserting the curved section into the outer tube to thereby adjust a direction of the nozzle head relative to a axis of the nozzle main body. In addition, a longitudinally extending gap exists between the outer tube and the nozzle. The gap functions as a discharge path for discharging gas within the body cavity.

13 Claims, 16 Drawing Sheets

APPLICATOR

This application is a continuation of International Application No. PCT/JP2009/053320 filed on Feb. 25, 2009, and claims priority to Japanese Application No. 2008-050371 filed on Feb. 29, 2008 and Japanese Application No. 2008-171828 filed on Jun. 30, 2008, the entire content of all three of which is incorporated herein by reference

TECHNICAL FIELD

The present invention generally relates to an applicator. More specifically, the invention pertains to an applicator insertable into a living body to eject or apply a liquid to a desired part of the living body.

BACKGROUND DISCUSSION

Methods are known by which two or more liquids are mixed and then injected to an affected part of a living body or the like, thereby forming an anti-adhesive agent, a living body tissue adhesive or the like. An applicator has been developed to perform this mixing and ejection.

This applicator is configured so that components which are coagulated when mixed, for example a solution containing thrombin and a solution containing fibrinogen, are sent to the vicinity of the affected part while being separated from each other and are applied to the affected part while being mixed.

A known applicator has two syringes each containing a different type of liquid, and a nozzle that mixes the liquids (hereinafter, referred to as "mixed liquid") from each syringe to expel the mixed liquid. Such an applicator is disclosed in Japanese Application Publication No. 2002-282368. The applicator described in this publication is configured so that the nozzle is connected with a gas supply source for supplying an aseptic gas to expel liquid together with the aseptic gas.

When the applicator described in the aforementioned application publication is used, for example in a laparoscopic surgery, the nozzle of the applicator is inserted into an abdominal cavity via a trocar tube detained (fixed) in an abdominal wall in advance. Since a direction toward which the nozzle faces is the same as the inserting direction when the nozzle is inserted into the living body, the mixed liquid can be expelled only toward this direction, that is only in one direction. Thus, in this known applicator, the mixed liquid can be applied to only a narrow range in the abdominal cavity, that is only a target part present in the one direction (the direction toward which the nozzle faces), and so the application of the mixed liquid over a wide range was impossible.

In the laparoscopic surgery, the aseptic gas is supplied into the abdominal cavity via the trocar tube. As a result, a gas abdominal pressure within the abdominal cavity rises, so that the abdominal cavity is expanded. The know applicator is configured so that the mixed liquid together with the aseptic gas is expelled from the nozzle as described above. Thus, the gas abdominal pressure within the abdominal cavity further rises due to the expelled aseptic gas, whereby the abdominal cavity is excessively expanded.

SUMMARY

The applicator disclosed here can relatively easily and reliably apply liquid or powder over a wide range and can suppress or prevent a rise in body pressure within a body cavity due to the expelled gas.

The applicator is used by being inserted into a living body, and includes a nozzle comprised of an elongated nozzle main body and a nozzle head through which liquid together with gas is expelled to deliver the liquid to a desired region in a body cavity of a living body. The nozzle head is positioned at a distal end side of the nozzle main body. The nozzle main body possesses a distal end portion that is curved or bent without application of a force to the distal end portion so that the distal end portion of the nozzle main body is configured as a curved section, with the curved section being flexible. An outer tube possesses a distal end and has a hollow interior sized to permit at least a portion of the nozzle main body to be positioned in the hollow interior of the outer tube. The outer tube and the nozzle main body are relatively movable so that the outer tube relatively moves along a longitudinal extent of the outer tube. Relative movement of the outer tube and the nozzle main body in a manner causing the proximal relative movement of the outer tube with respect to the nozzle main body, while a portion of the nozzle main body is in the hollow interior of the outer tube and the curved section extends distally beyond the distal end of the outer tube, causes the curved section to change its configuration and become more straightened to thereby adjust a direction of the nozzle head relative to an axis of the nozzle main body.

As a result, liquid or powder expelled from the nozzle head can be relatively easily and reliably applied over the wide range.

It is desirable that the outer tube has a front end opening portion in which a front end is opened to communicate with a longitudinally extending gap between the inner surface of the outer tube and the outer surface of the nozzle main body, and the front end opening portion functions as an inlet through which the gas within the body cavity flows into the gap.

As a result, the gas within the body cavity can relatively easily flow in the gap.

The outer tube preferably has at least one side hole formed on the wall portion and communicates with the gap, and the side hole functions as an outlet through which the gas passing through the gap flows out.

As a result, the gas within the gap can be discharged.

The outer tube can include a cover portion covering the side hole from the outer peripheral side of the outer tube.

As a result, when a proximal end portion of the outer tube is grasped with fingers to perform a movement operation, it is possible to reliably prevent the side hole from being blocked by the fingers, whereby the gas passing through the gap can further reliably be discharged via the side hole.

The applicator preferably has positioning means for positioning the outer tube with respect to the longitudinal direction of the nozzle.

This helps maintain a direction of the nozzle head relative to the axis of the nozzle main body.

The positioning means can include an elastic body which is fixed with respect to the outer peripheral surface of the nozzle main body or the inner peripheral surface of the outer tube at an intermediate portion of the gap and comes in contact with the other surface.

The elastic body can seal the gap, and this gap can communicate with a side hole in the outer tube at a position on the proximal end side of the elastic body.

The elastic body can also function to restrict a gap distance of the gap to inhibit or prevent that the inner peripheral surface of the outer tube from coming in contact with the outer peripheral surface of the nozzle main body, so that the middle of the gap is blocked, whereby the gas can be relatively reliably discharged via the gap.

It is desirable that the elastic body is ring-shaped and encircles the outer peripheral surface of the nozzle. It is thus possible to reliably perform the positioning of the outer tube relative to the longitudinal direction of the nozzle.

The positioning means can alternatively be in the form of a protruding portion which protrudes from either the outer peripheral surface of the nozzle main body or the inner peripheral surface of the outer tube at an intermediate portion of the gap and comes in contact with the other surface.

The applicator can be configured such that the elastic body is intermittently disposed in plural spaced apart locations along the outer peripheral direction of the nozzle. A portion of the gap positioned at the front end side of the elastic body and a portion of the gap positioned at the proximal end side of the elastic body communicate with each other via a portion of the gap where the elastic body is not installed, that is between the elastic bodies. Thus, the gas can enter the gap even from the front end opening portion of the sheath.

The nozzle head can also be provided with a fitting portion which is fitted to the front end opening portion of the outer tube when the axis of the nozzle head coincides with the axis of the nozzle main body.

This helps maintain a state in which the axis of the nozzle head coincides with the axis of the nozzle main body.

At least one groove can be formed in the fitting portion along the axial direction of the nozzle head, and when the axis of the nozzle head coincides with the axis of the nozzle main body, the gas within the body cavity flows in the gap via the groove.

As a result, even when the axis of the nozzle head coincides with the axis of the nozzle main body, the groove inhibits or prevents the overall front end opening portion of the outer tube from covering the nozzle head (blocking), whereby the gap communicates with the living body via the groove. As a result, the gas within the living body can reliably flow in the gap via the groove.

It is desirable for the curved section be curved to the degree that the nozzle head faces the proximal end side in a natural state of not giving an external force. As a result, it is possible to apply the liquid even to the proximal end side.

The curved section can exhibit a U-shape in the natural state, with the axis of the nozzle head and the axis of the nozzle main body being parallel with each other, and the nozzle being used such that a part of the curved section is accommodated in the outer tube, a degree of the curve of the curved section is made smaller than at the time of the natural state, and the liquid/powder and the gas are expelled from the nozzle head toward the proximal end side in this state.

As a result, it is possible to relatively easily apply the liquid/powder even to the proximal end side.

The nozzle main body has a liquid/powder flow path, which is connected to a liquid supply means for supplying the liquid and through which the liquid/powder from the supply means passes, and a gas flow path which is connected to a gas supply means for supplying the gas and through which the gas from the gas supply means passes. It is thus possible to collectively expel the gas and the liquid from the nozzle head.

According to another aspect, an applicator sized and configured to be inserted into a living body comprises a nozzle comprised of an elongated nozzle main body and a nozzle head through which liquid together with gas is expelled to deliver the liquid to a desired region in a body cavity of a living body, with the nozzle head positioned at the distal end side of the nozzle main body. The nozzle main body possesses a distal end portion that is curved or bent without application of a force to the distal end portion so that the distal end portion of the nozzle main body is configured as a curved section that is flexible. The nozzle head is positioned distal of the curved section and possesses a first axis, and the portion of the nozzle main body immediately proximal the curved section possesses a second axis that is not coincident with the first axis. An elongated outer tube has an interior open at a distal end of the outer tube and a open at a proximal end of the outer tube. At least a part of the nozzle main body is positioned in the interior of the hollow tube, with the curved section of the nozzle main body and the nozzle head extending distally beyond the distal end of the outer tube. The nozzle and the outer tube are relatively movable so that relative proximal movement of the outer tube with respect to the nozzle main body causes the distal end of the outer tube to contact the curved section and movably urge the curved section in a manner adjusting a direction in which the nozzle head faces. A longitudinally extending gap exists between the inner surface of the outer tube and the outer surface of the nozzle main body; and the gap communicates with outside the outer tube and functioning as a discharge path for discharging gas within the body cavity via the gap to the outside of the living body when a body pressure within the body cavity rises.

The applicator preferably includes an adjusting means for adjusting the discharging amount of the gas. As a result, for example, when the pressure in the living body is reduced, the discharging amount of the gas can be increased.

The adjusting means can includes the inner peripheral surface of the outer tube and a taper surface formed on the proximal end outer peripheral portion of the nozzle main body and having an outer diameter gradually increasing toward the proximal end direction. The adjusting means is operated by moving the outer tube so that the taper surface and the inner peripheral surface of the outer tube approach and are separated from each other, whereby the gap distance of the gap changes.

As a result, for example, when it is desired to reduce the pressure within the living body, the discharging amount of the gas can relatively easily be increased.

It is desirable that the nozzle be used while inserted into the trocar tube. By protruding the nozzle head of the nozzle from the trocar tube, the nozzle head can be relatively easily inserted into the living body.

The trocar tube preferably has a tubular body, a hub provided on the proximal end portion of the tubular body, and a valve main body provided on the hub and into which the nozzle is insertable.

In a case where the gas is supplied into the living body via the trocar tube, even in the state in which the nozzle is inserted into the trocar tube, it is possible to inhibit or prevent the gas from flowing out of the trocar tube, whereby the gas is effectively and reliably supplied into the living body.

The applicator preferably has restriction means for restricting the movement limitation of the outer tube with respect to the trocar tube in the front end direction.

This helps inhibit or prevent the proximal end portion of the outer tube from undesirably entering the trocar tube.

The trocar tube preferably has a tubular body and a hub provided on the proximal end portion of the tubular body, and the restriction means includes a protruding portion which protrudes from the proximal end outer peripheral portion of the outer tube and comes in contact with the proximal end portion of the hub.

As a result, it is possible to inhibit or prevent the proximal end portion of the outer tube from carelessly entering the trocar tube.

BRIEF DESCRIPTION OF THE DRAWING FIGURES

DETAILED DESCRIPTION

Set forth below is a detailed description of a first embodiment of the applicator disclosed here. For convenience in the description which follows, the left side in FIGS. 1-4 (also for FIGS. 7-17) is called the "front end" or "distal end' and the right side is called the "proximal end" or "rear end".

Figure 1:
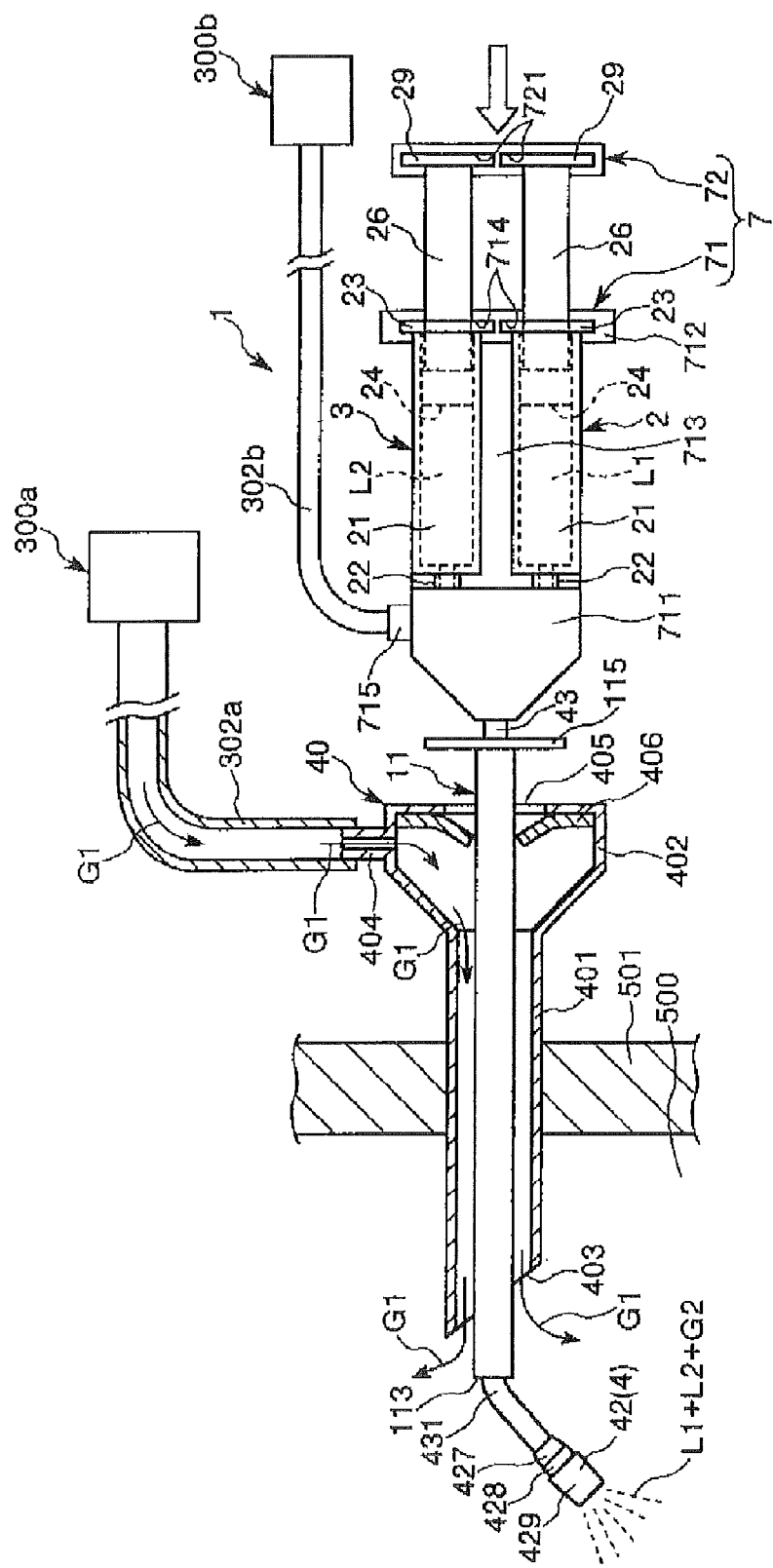
FIG. 1 is a somewhat schematic partial longitudinal cross-sectional view of a first embodiment of an applicator disclosed here in a use state.

FIG. 1 illustrates the applicator 1 inserted into an abdominal cavity 500, for example during laparoscopic surgery, to apply a mixture of two types of liquids with different liquid compositions (first liquid L1 and second liquid L2) to organs, the abdominal wall 501 or the like, while mixing the liquids. The insertion of the applicator 1 into abdominal cavity 500 is performed via a trocar tube 40 detained in the abdominal wall 501 in advance. Specifically, the nozzle 4 of the applicator 1 is inserted into the trocar tube 40 to protrude the nozzle head 42 of the nozzle 4 from (i.e., distally beyond) the trocar tube 40, whereby applicator 1 (nozzle head 42) can be inserted into the abdominal cavity 500.

Before describing the applicator 1, the trocar tube 40 will be described. As shown in FIG. 1, the trocar tube 40 has a main body portion (tubular body) 401 possessing a tubular shape, and a hub 402 provided on the proximal end portion of the main body portion 401.

The main body portion 401 refers to that portion of the tube at which the front end and the proximal end are opened. The front end (distal end) portion 403 of the main body portion 401 is sloped with respect to an axis of the main body portion 401. As a result, the front end portion of the trocar tube 40 exhibits a shape which makes it easier to insert the trocar tube 40 from the front end side into the abdominal cavity 500. Thus, it is possible to easily perform the insertion operation of the trocar tube 40 into the abdominal cavity 500.

The hub 402 is a part, which has an inner diameter and outer diameter larger than those of the main body portion 401, and communicates with the main body portion 401.

A gas supply port 402 protrudes on the outer peripheral portion of the hub 402. The gas supply port 404 is connected to a gas cylinder (gas supply means) 300a via a tube 302a. Gas (aseptic gas) G1 supplied from the gas cylinder 300a sequentially passes through the tube 302a, the gas supply port 404, the hub 402 and the main body portion 401, and is supplied into the abdominal cavity 500 (see FIG. 1). Due to the supply of gas G1, a gas abdominal pressure in the abdominal cavity 500 rises further than the atmospheric pressure by 8 to 12 mmHg, whereby the abdominal cavity 500 is expanded. As a result, the abdominal cavity 500 becomes a size which is sufficient for performing laparoscopic surgery. In addition, the gas cylinder 300a has the same configuration as the gas cylinder 300b, described later, and so a detailed description of the gas cylinder 300a will not be set forth here.

A duckbill valve (valve main body) 406 is installed on the proximal end opening portion 405 of the hub 402. The duckbill valve 406 covers the proximal end opening portion 405 of the hub 402. The duckbill valve 406 is closed in the state in which the applicator 1 is not inserted into the trocar tube 40, and is opened when the applicator 1 is inserted into the trocar tube 40. The duckbill valve 406 can prevent gas G1 from flowing out of the proximal end opening portion 405 of the hub 402, even in the state in which the applicator 1 is inserted. Thus, gas G1 is effectively and reliably supplied into the abdominal cavity 500.

The main body portion 401 and the hub 402 may be formed integrally, and may be configured separately, so that the separated bodies are connected and fixed to each other.

Figure 2:
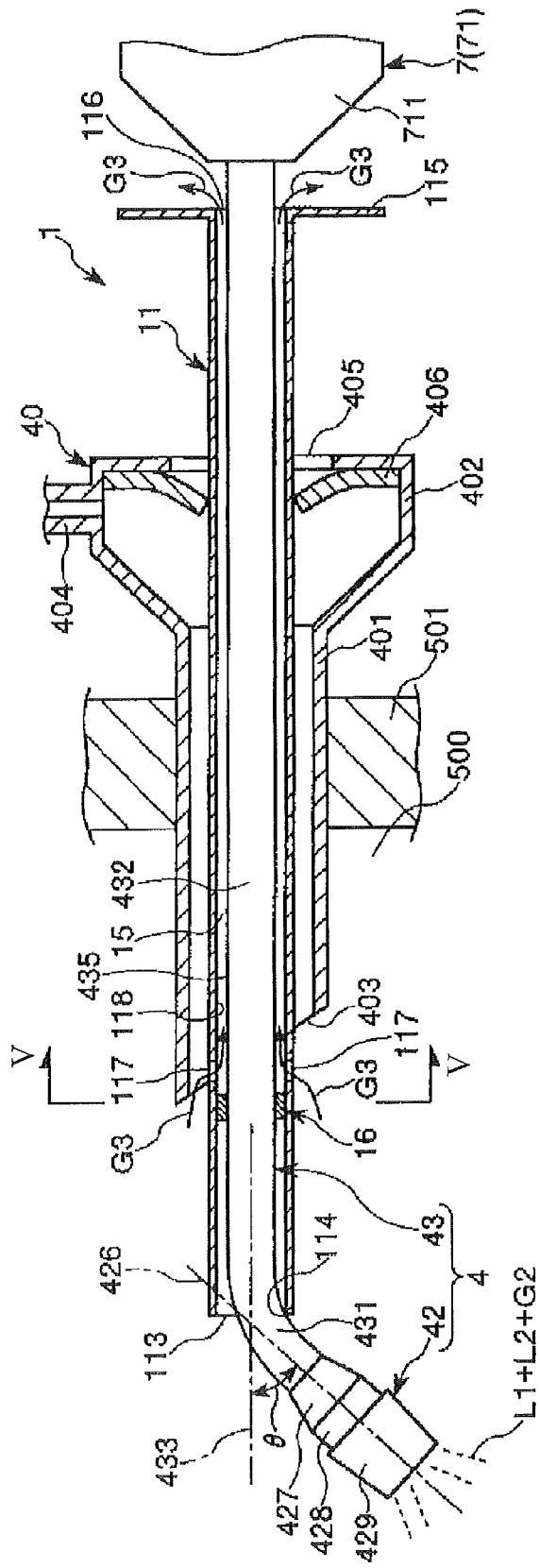
FIG. 2 is an enlarged partial longitudinal cross-sectional view of a portion of the applicator shown in FIG. 1 in one operational position.
Figure 3:
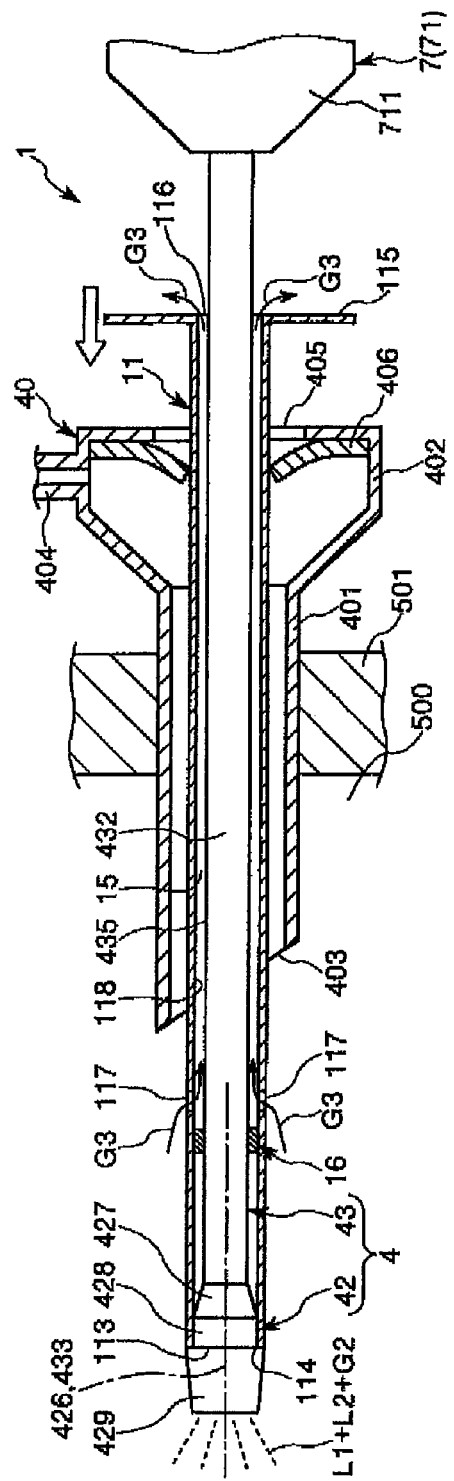
FIG. 3 is an enlarged partial longitudinal cross-sectional view of a portion of the applicator shown in FIG. 1 in another operational position.

As described above, the applicator 1 applies to the desired location the two types of liquids with different liquid compositions (first liquid L1 and second liquid L2) while mixing them (see FIGS. 1 to 3). The applicator 1 is used by loading a first syringe (liquid supply means) 2 containing a first liquid L1 and a second syringe (liquid supply means) 3 containing second liquid L2. Since the first syringe 2 and the second syringe 3 have substantially the same configuration, the first syringe 2 will be described below, and it is to be understood that the same description applies to the second syringe.

The first syringe 2 includes an outer case 21, a gasket 24 capable of sliding in the outer case 21, and a pusher 26 for moving and operating the gasket 24 along a longitudinal direction (an axial direction) of the outer case 21. The gasket 24 is connected to the front end of the pusher 26.

The outer case 21 is a cylindrical member with a bottom and a reduced diameter portion (a mouth portion) 22, which is reduced in inner and outer diameter with respect to the body portion of the outer case 21. The reduced diameter portion integrally protrudes and formed on a center portion of a front end side bottom portion of the outer case 21.

A flange 23 is integrally formed on a rear end outer periphery of the outer case 21. Gradations which indicate liquid amounts are provided on the outer peripheral surface of the outer case 21.

The materials forming the outer case 21 are not limited, though various resins as described with respect to the trocar tube 40 can be used as examples. In addition, it is desirable for the construction materials of the outer case 21 to be substantially transparent to permit visibility of the inner part.

The gasket 24 is formed of an elastic material and is accommodated in the outer case 21. The outer peripheral surface of the gasket 24 comes into close contact with the inner peripheral surface of the outer case 21 while sliding, so that the first liquid L1 can be pushed toward the mouth portion 22 while reliably maintaining a liquid-tight property in the outer case 21.

The movement of the gasket 24 is performed by moving and operating the pusher or plunger 26. The pusher 26 is an elongated member, and has a disk-shaped flange 29 at one end.

Before the first syringe 2 is loaded into the applicator 1, the first liquid L1 is charged in a space (a liquid containing space) surrounded by the outer case 21 and the gasket 24. In the second syringe 3, the second liquid L2 is charged in a space (a liquid containing space) surrounded by the outer case 21 and the gasket 24.

The first liquid L1 charged in the first syringe 2 and the second liquid L2 charged in the second syringe 3 are different from each other in composition (ingredients).

The first liquid L1 and the second liquid L2 are suitably selected depending upon the use, the purpose, an index case of the applicator 1 or the like. For example, when the liquids are intended to administer a living body tissue adhesive, one of first liquid L1 and second liquid L2 can be a liquid containing thrombin, and the other liquid can be a liquid containing fibrinogen.

When the first liquid L1 and the second liquid L2 are used for administering an anti-adhesive agent, one of them can be a liquid containing carboxylmethyl dextrin modified with succinimidyl radical, and the other of them can be a liquid containing disodium dihydrogen phosphate which is a pH regulator.

The first liquid L1 and the second liquid L2 in this combination gel or solidify when they are mixed with each other. Due to this gelling, for example, the mixture (hereinafter, often called "mixture") of the first liquid L1 and the second liquid L2 can reliably remain in the applied living body tissue (i.e., at the target part). In addition, since the mixture reliably remains in the target part, a function as the living body tissue adhesive or the anti-adhesive agent can reliably be exhibited in the target part.

It is understood that the types or the combinations of the first liquid L1 and the second liquid L2 are not limited to the above description.

The first syringe 2 and the second syringe 3 are connected to the nozzle 4 as described later and, upon pressing and operating the respective pushers 26, they can easily and reliably supply the first liquid L1 to a first flow path 44 of the nozzle 4 and a second liquid L2 to a second flow path 45. The pressing operations of the respective pushers 26 are manually performed by an operator of the applicator 1. For this reason, the operator can perform the application of the mixture at his own arbitrary timing.

The applicator 1 expels the first liquid L1 and the second liquid L2 together with gas G2 as illustrated in FIGS. 1-3. Due to the presence of the gas G2, the mixture is atomized, whereby the mixture can uniformly be applied to the target part. Gas G2 is supplied by a gas cylinder 300b. Gas cylinder 300b is connected with the nozzle via a tube 302b.

Gas cylinder 300b has the compressed aseptic gas G2 (hereinafter, called "gas G2") charged in an inner space of the cylinder and can supply gas G2 flowing at a high speed to the applicator 1 (nozzle 4). In the middle of the gas cylinder 300b or the tube 302b, an openable and closable valve (not shown), which controls the supply/the supply stop of gas G with respect to applicator 1, is installed. When applying the mixture, the valve is in the open state.

As shown in FIGS. 1-3, the applicator 1 includes an applicator main body 7, a nozzle 4 provided on the front end side of the applicator main body 7, and a sheath (outer tube) 11 through which nozzle 4 is inserted.

As shown in FIG. 1, the applicator main body 7 includes a syringe holding portion 71, which holds the outer case 21 of the first syringe 2 and the outer case 21 of the second syringe 3, and a flange connecting portion 72 which connects the flange 29 of the pusher 26 of the first syringe 2 with the flange 29 of the pusher 26 of the second syringe 3.

The syringe holding portion 71 fixes the first syringe 2 (outer case 21) and the second syringe 3 (outer case 21) in parallel. The syringe holding portion 71 has a fitting portion 711 to which the mouth portion 22 of each outer case 21 is fitted, an inserting portion 712 which is situated at the proximal end side of the fitting portion 711 and into which an edge portion of flange 23 of each outer case 21 is positioned, and a connecting portion 713 connecting the fitting portion 711 with the inserting portion 712.

When the mouth portion 22 of each outer case 21 is fitted to the fitting portion 711, the mouth portion 22 of the first syringe 2 is connected to the first flow path 44 of the nozzle 4, and the mouth portion 22 of the second syringe 3 is connected to the second flow path 45. As a result, referring to FIG. 4, it is possible to supply the first liquid L1 to the first flow path 44 and the second liquid L2 to the second flow path 45.

Figure 4:
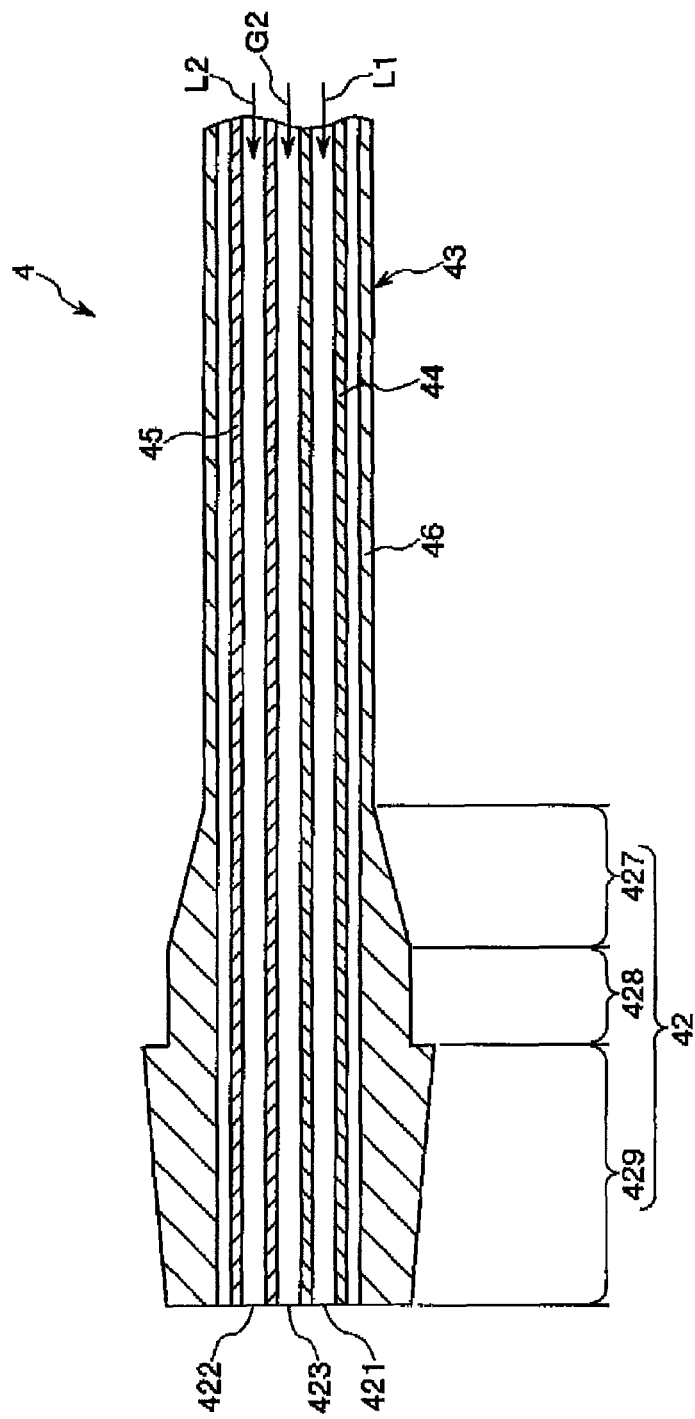
FIG. 4 is a longitudinal cross-sectional view of a front end side portion of the nozzle in the applicator in FIG. 1.

On the outer peripheral portion of the fitting portion 711, the connection portion 715 protrudes and is connected to an end portion of the tube 302b through which gas G2 from the gas cylinder 300b passes. When the tube 302b is connected to the connection portion 715, the tube 302b is connected to the third flow path 46 of the nozzle 4. As a result, it is possible to supply gas G2 to the third flow path 46 as shown in FIG. 4.

The inserting portion 712 includes grooves 714 in which is positioned the edge portion of the flange 23 of the outer case 21.

In the syringe holding portion 71, the mouth portions 22 of each outer case 21 is fitted to the fitting portion 711, and the flange 23 of the outer case 21 is inserted into the inserting portion 712 (the grooves 714), whereby each outer case 21 can reliably be maintained.

The flange connecting portion 72 is a plate-shaped member that connects the flange 29 of the pusher 26 of the first syringe 2 with the flange 29 of the pusher 26 of the second syringe 3. Grooves 721 are formed on the flange connecting portion 72. The grooves 721 receive the edge portions of the flanges 29 of each pusher 26. By pressing the flange connecting portion 72 toward the front end direction, each pusher 26 can collectively be moved toward the front end direction. In this manner, when the applicator 1 is used, that is when the mixture is applied to the target part such as an affected living body part, the flange connecting portion 72 functions as an operating portion which is pressed and operated by the user.

Materials for forming the syringe holding portion 71 and the flange connecting portion 72 include, for example, various resins materials.

The nozzle 4 is installed on the front end side of the applicator main body 7. The nozzle 4 expels gas G2 together with the first liquid L1 and the second liquid L2 (mixture).

As shown in FIGS. 2-4, the nozzle 4 is comprised of the nozzle main body 43 and the nozzle head 42 provided on the front end of the nozzle main body 43. The nozzle main body 43 exhibits a longer length than the nozzle head 42.

As shown in FIG. 4, the nozzle main body 43 has first a flow path 44 through which the first liquid L1 from the first syringe 2 passes, a second flow path 45 through which the second liquid L2 from the second syringe 3 passes, and the third flow path 46 through which the gas G2 from the gas cylinder 300b passes.

The first flow path 44 and the second flow path 45 are respectively formed as inner tubes. The front end (distal end) of each tube extends up to the front end surface of the nozzle head 42 and opens at the front end (distal end). In the nozzle head 42, the opening portion of the inner tube constituting the first flow path 44 functions as a first discharging port 421 for discharging the first liquid L1, and the opening portion of the inner tube constituting the second flow path 45 functions as a second discharging port 422 for discharging the second liquid L2. The inner tube constituting the first flow path 44 extends up to a position where the proximal end portion of the inner tube is connected to the mouth portion 22 of the first syringe 2. Similarly, the inner tube forming the second flow path 45 extends up to a position where the proximal end portion of the inner tube is connected to the mouth portion 22 of the second syringe 3.

The third flow path 46 is constituted by an outer tube, which is situated on the outer periphery side of the inner tubes which respectively constitute the first flow path 44 and the second flow path 45. That is, both of the inner tubes pass through the outer tube forming the third flow path 46 and are surrounded by the outer tube. The outer tube is configured so that the front end extends up to the front end surface of the nozzle head 42 and opens at the front end surface. In the nozzle head 42, the opening portion of the outer tube functions as a third discharging port 423 for expelling gas G2. In addition, the outer tube extends up to a position where the proximal end portion of the outer tube is connected to the tube 302b via the connection portion 715 of the applicator main body 7.

The respective inner tube and the outer tube are in the positional relationship described above. Thus, on the outer peripheral sides of first discharging port 421 and second discharging port 422, that is in order to surround the first discharging port 421 and the second discharging port 422, a third discharging port 423 is provided. That is, the third discharging port 423 surrounds the first and second discharge ports 421, 422. As a result, the first liquid L1 discharged from the first discharging port 421 and the second liquid L2 discharged from the second discharging port 422 are mixed with gas G2 discharged from the third discharging port 423 at a high speed. At this time, the first liquid L1 and the second liquid L2 are respectively atomized and expelled. As a result, the first liquid L1 and the second liquid L2 are reliably mixed with each other and are applied to the affected part.

As shown in FIGS. 1 and 2, the front end portion of the nozzle main body 43 has a curved section 431, which is curved or bent and has flexibility. This section of the nozzle main body 43 which is curved/bent is hereinafter generally referred to as a curved section for ease in description. The curved section 431 exhibits the curved/bent shape in the absence of a force applied to the curved section. That is, in the natural state shown in FIG. 1 in which the front end portion (distal end portion) of the nozzle main body 43 protrudes distally beyond the front end opening portion 113 of the sheath 11 with no force applied to the distal end portion of the nozzle main body 43, the distal end portion of the nozzle main body 43 exhibits the curved section 431. The curved section results in the axis 426 of the nozzle head 42 forming an angle (internal angle greater than zero degrees and less then 180 degrees) relative to the axis 433 of the portion of the nozzle main body 430 immediately proximal of the curved section).

In the illustrated embodiment, the curved section 431 is curved or bent so that the front end of the curved section faces obliquely downward. Due to the curved section 431, the axis 426 of the nozzle head 42 slopes (is angled) with respect to the axis (strictly speaking, the axis of the portion 432 of the proximal end side further than curved section 431 of the nozzle main body 43) 433 of the nozzle main body 43 as shown in FIG. 2.

When the curved section 431 is curved or bent without being restricted by the sheath 11 (described later), the angle θ between the axis 426 of the nozzle head 42 and the axis 433 of the nozzle main body 43 (hereinafter referred to as slope angle) is less than 180°, preferably about 30° to 90°, and more preferably about 45° to 70°.

The curved section 431 of the nozzle main body 43 is formed of a soft material, an elastic material or the like. In addition, the portion 432 of the nozzle main body 43 that is more proximal than the curved section 431 of the nozzle main body 43 may be formed of a rigid material, a soft material, or may be formed of an elastic material or the like and may have flexibility.

The curved section 431 and the portion 432 of the nozzle main body 43 on the proximal end side of the curved section 431 of the nozzle main body 43 may be configured so that they are formed of separated members and are fixed by bonding, melting or the like, and may be configured by being integrally formed.

The construction material forming the nozzle 4 (nozzle main body 43) includes, for example, various thermoplastic elastomers such as polyurethane base, polyester base, polyamide base, olefin base, and styrene base. The portion 432 of the nozzle main body on the proximal end side of the curved section 431 can be made of any of those materials. Examples of the material for forming the curved section 431 include the soft material and the elastic material.

As described above, the nozzle head 42 is that part of the nozzle from which the first liquid L1 is discharged from first discharging port 421, from which the second liquid L2 is discharged from second discharging port 422, and from which the gas G2 is expelled from third discharging port 423 while mixing the liquids.

The nozzle head 42 has a cylindrical outer shape, and has a first taper portion 427 with a gradually increasing outer diameter toward the front end direction, an outer diameter constant portion 428 with a constant outer diameter along a longitudinal direction (axial direction along the axis 426), and a second taper portion 429 with a gradually decreasing outer diameter toward the front end direction, which are disposed from the proximal end side toward the distal end side in this order.

The first taper portion 427 is formed so that when the nozzle 4 changes from the state shown in FIG. 2 to the state shown in FIG. 3, the inner edge portion 114 of the front end opening portion 113 of the sheath 11 can smoothly move along the first taper portion 427. As a result, the nozzle head 42 can be reliably introduced into the sheath 11. In addition, it is desirable that the edge portion 114 be spherical. As a result, the edge portion 114 can further smoothly move along the first taper portion 427.

The second taper portion 429 is situated on the front end side (distal end side) of the first taper portion 427. The second taper portion 429 is formed so that, for example, when the applicator 1 is inserted into the trocar tube 40 in the state shown in FIG. 3, the second taper portion 429 can smoothly pass through the duckbill valve 406 of the trocar tube 40. As a result, the inserting operation of the applicator 1 into the trocar tube 40 can be relatively easily performed. Further, the outer diameter of the proximal end of the second taper portion 429 is larger than the inner diameter of the sheath 11. As a result, it is possible to inhibit or prevent the nozzle head 42 from entering the sheath 11. That is, the front end of the nozzle head 42 is inhibited or prevented from moving toward the proximal end side further than the front end of the sheath 11 as shown in FIG. 3.

The outer diameter constant portion 428 is situated between the first taper portion 427 and the second taper portion 429. The outer diameter of the outer diameter constant portion 428 is the same as the outer diameter (maximum outer diameter) of the front end of the first taper portion 427, and is equal to or slightly larger than the inner diameter of the sheath 11. As a result, as shown in FIG. 3, when the axis 426 of the nozzle head 42 coincides with the axis 433 of the nozzle main body 43, the outer diameter constant portion 428 (also including the front end of the first taper portion 427) enters and is fitted to the front end opening portion 113 of the sheath 11. Thus, it is possible to maintain the state in which the axis 426 of the nozzle head 42 coincides with the axis 433 of the nozzle main body 43. The mixture can be applied to the target part within abdominal cavity 500 in the maintained state. In the applicator 1, the outer diameter constant portion 428 and the front end of the first taper portion 427 can be referred to as "a fitting portion" which is fitted to front end opening portion 113 of the sheath 11.

As shown in FIG. 2, similar to the illustrations in FIGS. 1 and 3, the applicator 1 has the sheath 11 which operates as a form restricting or controlling member that restricts or permits control of the shape of the curved section 431 of nozzle main body 43. The sheath 11 is formed as a tubular body with an elongated shape in which the front end and the proximal end of the tubular body are respectively opened, and the nozzle 4 (nozzle main body 43) is inserted into the sheath 11. In the present embodiment, the sheath 11 is adapted to cover or surround the nozzle from the portion (the outer diameter constant portion 428 of the nozzle head 42) on the front end side (distal side) of the curved section 431 up to the vicinity of the proximal end portion of the nozzle main body 43. The sheath 11 is adapted to be movable along the longitudinal direction of nozzle main body 43 with respect to the nozzle main body 43.

It is desirable that the sheath 11 be formed of a rigid material and have necessary and sufficient stiffness so that it can restrict the shape of the curved section 431 when covering a part or all of the curved section 431, as well as having a low sliding property.

The materials which can be used to form the sheath 11 include a polyolefin resin such as polyethylene or polypropylene, a fluorine resin such as polytetra fluoroethylene, and a rigid resin such as polycarbonate, polyethylene terephthalate or polyamide.

As described above, the sheath 11 can be moved and operated along the longitudinal direction of nozzle main body 43. Due to the movement operation, the curved section 431 is inserted into the sheath 11, and the protrusion length of the curved section 431 from the front end of sheath 11 is adjusted, whereby the angle of curved section 431 can be changed as shown in FIGS. 2 and 3. As a result, the slope angle θ (the direction of the nozzle head 42) of the axis 426 of the nozzle head 42 with respect to the axis 433 of the nozzle main body 43 can be adjusted. In other words, the sheath 11 can move between a first position (slope angle θ=0°) where the curved section 431 is restricted by the sheath 11 and possesses a linear shape and the direction of the axis 426 of the nozzle head 42 coincides with the direction of the axis 433 of the nozzle main body 43 (i.e., the axis 426 of the nozzle head 42 and the axis 433 of the nozzle main body 43 are coincident) as shown in FIG. 3, and a second position (slope angle θ is the maximum slope angle) where the curved section 431 exhibits the curved or bent state without being restricted by the sheath 11, with the axis 433 of the nozzle main body 43 sloping (i.e., forming an angle other than zero and other than 180°) with respect to the axis 426 of the nozzle head 42 as shown in FIG. 2. As a result, by moving the sheath 11 to a predetermined position between the first position and the second position, slope angle θ can be freely adjusted within the range from 0° to the maximum slope angle.

As described above, it is possible to spray the mixture from the nozzle head 42 toward a plurality of places (over a relatively wide area) within the abdominal cavity 500 (for example, the organ or abdominal wall 501), while changing the slope angle θ of the nozzle head 42 by moving the sheath 11 to suitably adjust the slope angle θ. Thus, the applicator 1 can easily and reliably apply the mixture in the abdominal cavity 500 over a wide range. In addition, in the applicator 1, the mixture can be applied relatively evenly to the rear side of the abdominal wall 501 which faces the organ positioned in the inserting direction of the applicator 1 into the living body, by suitably setting (e.g., a "U" shape) a degree (slope angle θ) of the curve of the curved section 431 in the natural state in which the external force is not applied.

The proximal end outer peripheral portion of the sheath 11 has the protruding plate-shaped flange 115. The sheath 11 can be moved and operated by grasping the flange 115 and moving the flange in the longitudinal direction of the sheath 11. In this manner, the flange 115 functions as an operating portion when moving the sheath 11.

As described above, the applicator 1 is used in the state of being inserted into the trocar tube 40. In this state, when the applicator 1 is gradually pressed or pushed toward the front end direction relative to the tube 40, the flange 115 of the sheath 11 comes into contact with the proximal end opening portion 405 of the hub 402. As a result, the movement limitation of the sheath 11 with respect to the trocar tube 40 in the forward direction is restricted, which makes it possible to help prevent the proximal end portion of the sheath 11 from unintentionally entering the trocar tube 40. That is, this helps prevent the proximal end portion of the sheath 11 from moving to the front end side further than the proximal end opening portion 405 of the trocar tube 40. As a result, the proximal end portion of the sheath 11 can reliably protrude from the proximal end opening portion 405 of the trocar tube 40 to grasp the protruded portion. Thus, the sheath 11 can be moved and operated. In this manner, the flange 115 also functions as a restriction means that restricts the movement limitation of the sheath 11 with respect to the trocar tube 40 in the front end (forward) direction.

In addition, the operation for adjusting the slope angle θ and the operation for discharging (expelling) the first liquid L1 and the second liquid L2 can be performed in any order.

That is, the operation for adjusting the slope angle θ and the operation for expelling the first liquid L1 and the second liquid L2 may concurrently be performed, and the operation for expelling the first liquid L1 and the second liquid L2 begins first, and then, the operation for adjusting the slope angle θ may be performed. In this case, after the first liquid L1 and the second liquid L2 begin to be expelled, the range of performing the application of the liquids can be widened by the adjustment of the slope angle θ. In addition, the operation for adjusting the slope angle θ can be performed first, and then the operation for expelling the first liquid L1 and the second liquid L2 may be performed.

Incidentally, as shown in FIGS. 2 and 3, a gap 15 is formed between the inner surface of the sheath 11 and the outer surface of the nozzle 4. The gap 15 extends along the longitudinal direction of the sheath 11, that is from the front end opening portion 113 of the sheath 11 to the proximal end opening portion 116.

The sheath 11 has two side holes (through holes) 117 passing through the wall portion. The side holes 117 are located on the proximal side of the front end opening portion 113. The side holes 117 are oppositely disposed (diametrically positioned) at the same position with respect to the longitudinal extent of the sheath 11. Each side hole 117 communicates with the gap 15 and function as inlet through which gas G3 within the abdominal cavity 500 flows in the gap 15 as apparent from FIGS. 2 and 3. That is, the side holes 117 communicate with the gap 15 and serve as blow-in ports through which the gas G3 is blown in. The number of side holes 117 is not limited to two. For example, the number of side holes may be one, or three or more.

The gap 15 functions as a discharge path for discharging gas G3 within the abdominal cavity 500 from the body. This is described below. The gap 15 is preferably dimensioned to achieve the desired amount of gas discharge from the body cavity. The gap 15 preferably has a radial dimension of at least 0.2 mm, more preferably at least 0.3 mm. In the illustrated embodiment, the radial dimension of the gap 15 is preferably defined by one-half the difference between the inner diameter of the outer tube and the outer diameter of the nozzle main body. In the illustrated embodiment, the inner diameter of the outer tube is 4.5 mm and the outer diameter of the nozzle main body is 3.7 mm, so the radial dimension of the gap 15 is 0.4 mm.

As shown in FIG. 1, gas G1 is expelled from the trocar tube 40 into the abdominal cavity 500, and gas G2 together with the liquid mixture is expelled from the applicator 1. As described above, due to the gas G1, the gas abdominal pressure within the abdominal cavity 500 rises and the abdominal cavity 500 expands. The gas abdominal pressure within the abdominal cavity 500 also rises due to the gas G2, whereby the abdominal cavity 500 tries to further expand. However, the discharging gas G3 (including the gases G1 and G2) within the abdominal cavity 500 flows in the gap 15 via each side hole 117 as shown in FIGS. 2 and 3. The discharging gas G3 flows down in the gap 15 and is discharged from the proximal end opening portion 116 as generally shown in FIGS. 2 and 3. As a result, an excessive rise in gas abdominal pressure within the abdominal cavity 500 can be suppressed (or prevented), which can help inhibit or prevent the abdominal cavity 500 from trying to further expand.

As described above, the applicator 1 is configured so that it can relatively easily and reliably apply the liquid mixture within the abdominal cavity 500 over a relatively wide range or region/area. Since the liquid mixture is applied within the abdominal cavity 500 over the wide range, the expelling amount of the mixture also increases, and the expelling amount of gas G2 also increases. When a large amount of gas G2 is expelled, the gas abdominal pressure in the abdominal cavity 500 seems to be increased; however, the exhausting operation performed by the gap 15 helps suppress this rise. In this manner, the applicator 1 is effective even in a case where the mixture is applied within the abdominal cavity 500 over the wide range.

Figure 5:
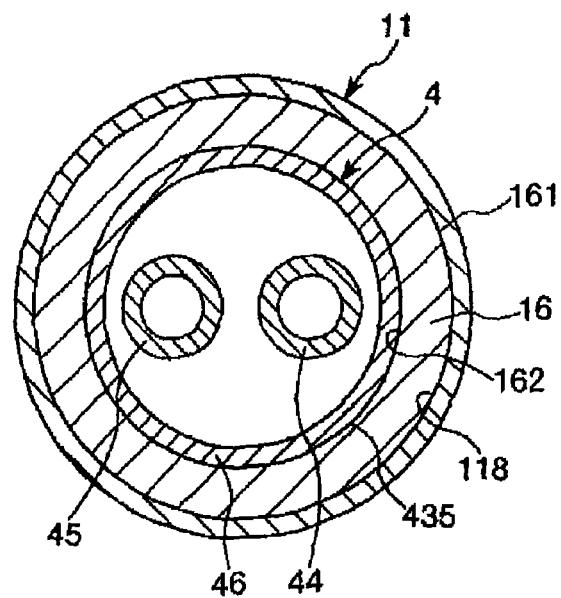
FIG. 5 is a transverse cross-sectional view of the nozzle and outer tube taken along the section line V-V in FIG. 2.

A ring-shaped or annular spacer 16 is installed at a longitudinally intermediate portion of the gap 15 and is positioned along the outer peripheral portion of the nozzle 4 as shown in FIGS. 2, 3 and 5. In one embodiment, the outer peripheral surface 161 of the spacer 16 is in contact with and fixed to the inner peripheral surface 118 of the sheath 11 (the spacer 16 and the sheath 11 move together as a unit), and the inner peripheral surface 162 of the spacer 16 is in contact with the outer peripheral surface 435 of the nozzle main body 43 as shown in FIG. 5. When the sheath 11 moves, the inner peripheral surface 162 of the spacer 16 slides on the outer peripheral surface 435 of the nozzle main body 43, whereby a frictional resistance is generated between the outer peripheral surface 435 of the nozzle main body 43 and the inner peripheral surface 162 of the spacer 16.

The spacer 16 with this configuration functions as a positioning means that positions the sheath 11 with respect to the longitudinal extent of the nozzle 4 in the stop position, when the sheath 11 is caused to move and stop. That is, when a force is applied to the sheath 11 to move the sheath 11 relative to the nozzle, and then the force is removed, the spacer 16 stops relative movement of the sheath and the nozzle 4, and fixes the position of the sheath 11 relative to the spacer 16. As a result, the slope angle θ of the nozzle head 42 can be maintained at the desired angle, so that the mixture can be expelled in this state.

The spacer 16 is installed between the inner peripheral surface 118 of the sheath 11 and the outer peripheral surface 435 of the nozzle main body 43 in the compressed state. The spacer 16 is not easily deformed in the diametrical direction and so the spacer exhibits characteristics maintaining the gap distance of the gap 15 (i.e., maintaining the spacing between the inner peripheral surface 118 of the sheath 11 and the outer peripheral surface 435 of the nozzle main body 43). As a result, the inner peripheral surface 118 of the sheath 11 does not contact (i.e., remains spaced from) the outer peripheral surface 435 of nozzle main body 43 so that it is possible to reliably prevent the gap 15 (the exhaust path) from being blocked, thus reliably exhausting the gas G3 via the gap 15.

As shown in FIG. 2, the spacer 16 is disposed on the front end side (distal side of the side holes 117. In this position, the spacer 16 seals the gap 15. In the state shown in FIG. 3, although the nozzle head 42 blocks the front end opening portion 113 of the sheath 11, since the gas G3 enters the gap 15 from each side hole 117, gas G3 can reliably be discharged.

The material forming the spacer 16 is not particularly limited. Examples of materials include various elastic materials such as those described regarding the duckbill valve 406.

Figure 6:
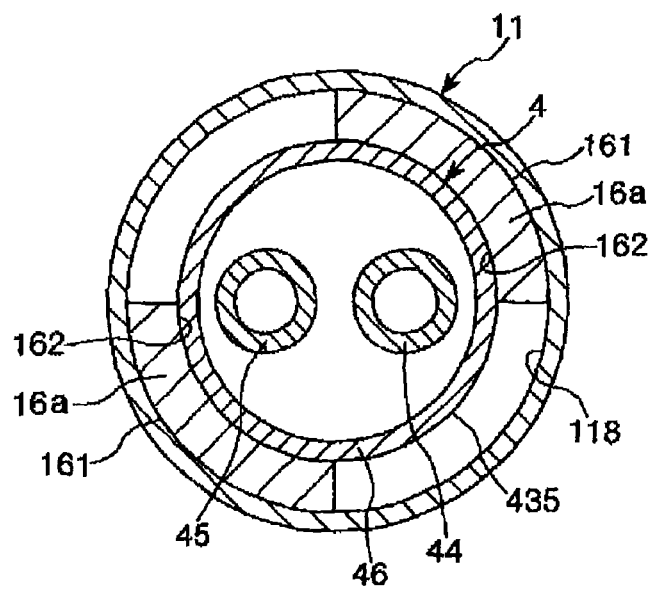
FIG. 6 is a transverse cross-sectional view of a nozzle and an outer tube in an applicator according to a second embodiment disclosed here.

FIG. 6 illustrates the nozzle and outer tube in an applicator according to a second embodiment. The following description of the second embodiment of the applicator focuses primarily on aspects of the applicator which differ from those associated with the above-described embodiment. Features associated with the second embodiment of the applicator that are the same as in the first embodiment are identified by common reference numerals and a detailed discussion of such features is not repeated here.

This embodiment is the same as the above-described first embodiment except for the arrangement state of the elastic body.

As shown in FIG. 6, multiple spacers 16a, which function as a positioning means for longitudinally positioning the sheath 11 with respect to the nozzle 4, are positioned circumferentially around the axis of the nozzle 4 (along the outer peripheral extent of the nozzle 4). In the illustrated embodiment, two spacers 16a are provided. Each spacer 16a has an arcuate shape and is disposed around the outer circumference of the nozzle 4 at equal angular distances. As a result, a portion of the gap 15 on the front end side of the spacer 16a and a portion of the gap 15 on the proximal end side of the spacer 16a communicate with each other via a portion of gap 15 where spacer 16a is not provided, namely between spacers 16a. As a result, in the state in which the front end opening portion 113 of the sheath 11 is not sealed by the nozzle head 42 (the state shown in FIG. 2), the gas G3 enters the gap 15 even from the front end opening portion 113 other than the side holes 117. Gas G3 is discharged from the proximal end opening portion 116. In this manner, in the present embodiment, front end opening portion 113 functions as an inlet through which gas G3 within the abdominal cavity 500 flows in the gap 15.

Furthermore, in the present embodiment, the discharging amount of gas G3 can be adjusted. Specifically, when the sheath 11 moves in the front end direction from the state shown in FIG. 2, the outer peripheral surface of the first taper portion 427 of the nozzle head 42 and the inner peripheral surface 118 of the sheath 11 approach each other. On the other hand, when the sheath 11 moves from this state in the proximal end direction, the outer peripheral surface of the first taper portion 427 of the nozzle head 42 is separated from the inner peripheral surface 118 of the sheath 11. This approaching and separation movement causes the gap distance of the gap 15 near the front end opening portion 113 of the sheath 11 to change. As a result, the inflow amount of gas G3 flowing in from the front end opening portion 113 is adjusted, and consequently, the discharging amount of gas G3 can be adjusted. As a result, for example, in a case where it is desired to reduce the gas abdominal pressure in the abdominal cavity 500, by operating the sheath 11 so that the outer peripheral surface of the first taper portion 427 of the nozzle head 42 is separated (more separate or farther spaced) from the inner peripheral surface 118 of the sheath 11, the discharging amount of the gas G3 can be improved (increased).

In this manner, in the present embodiment, the outer peripheral surface of the first taper portion 427 of the nozzle head 42 and the inner peripheral surface 118 of the sheath 11 form an adjusting means for adjusting the discharging amount of the gas G3.

Figure 7:
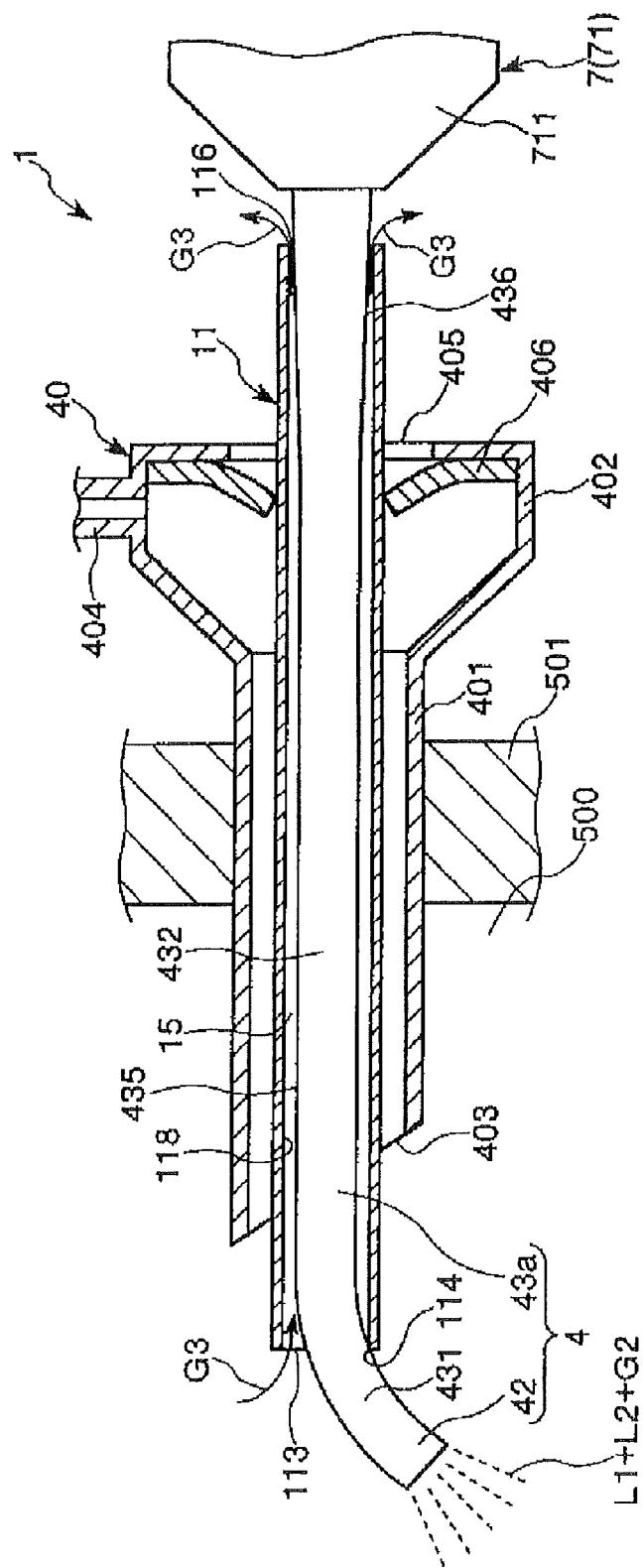
FIG. 7 is an enlarged partial longitudinal cross-sectional view of an applicator according to a third embodiment.
Figure 8:
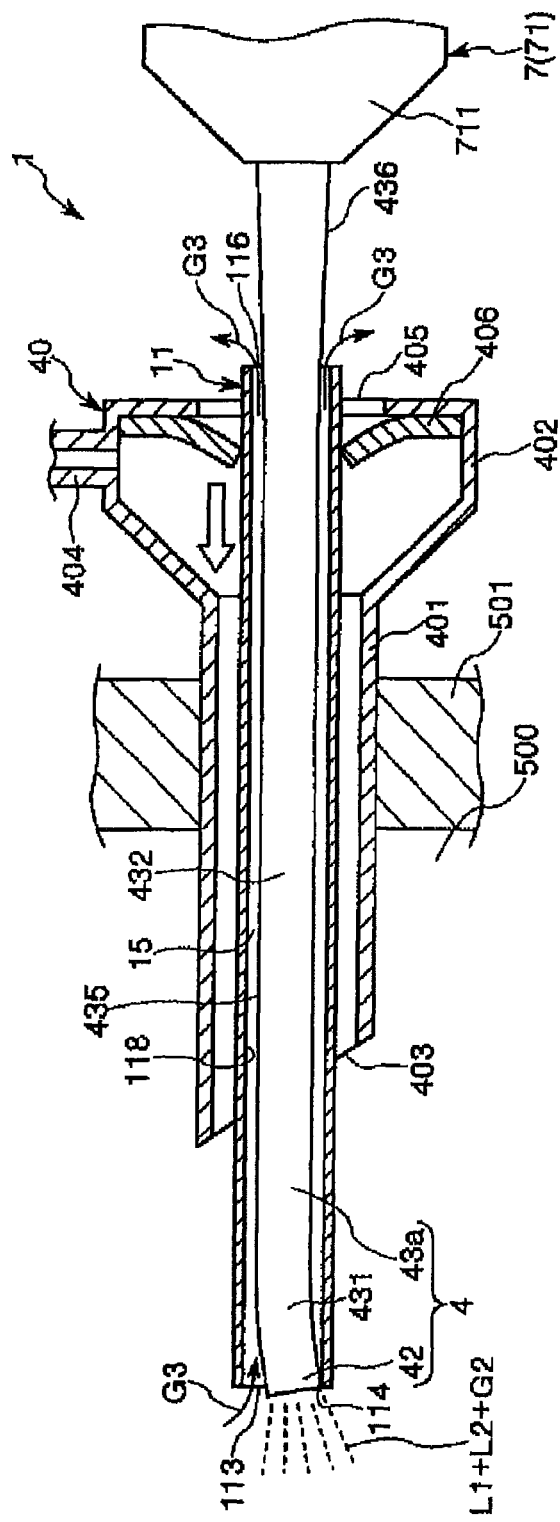
FIG. 8 is an enlarged partial longitudinal cross-sectional view of an applicator according to the third embodiment.

FIGS. 7 and 8 illustrate an applicator according to a third embodiment disclosed here. The following description of the third embodiment of the applicator focuses primarily on aspects of the applicator which differ from those associated with the above-described embodiments. Features associated with the third embodiment of the applicator that are the same as features in the above-described embodiments are identified by common reference numerals and a detailed discussion of such features is not repeated here.

This third embodiment of the applicator is the same as the first embodiment, except that the shape of the nozzle and the configuration of the outer tube differ.

As shown in FIGS. 7 and 8, a taper surface 436 is formed on the proximal end outer peripheral portion of the nozzle main body 43a. The taper surface 436 possesses an outer diameter gradually increasing toward the proximal end direction.

When the sheath 11 moves in the front end direction (forward direction) from the state shown in FIG. 7, the taper surface 436 of the nozzle main body 43a is separated from the inner peripheral surface 118 of the sheath 11 as seen in FIG. 8. On the other hand, when the sheath 11 moves in the proximal end direction from the state shown in FIG. 8, the taper surface 436 of the nozzle main body 43a approaches the inner peripheral surface 118 of the sheath 11. This approaching and separating movement causes a change in the gap distance of the gap 15 near the proximal end opening portion 116 of the sheath 11. As a result, the outflow amount of the gas G3 flowing out of the proximal end opening portion 116 is adjusted, and consequently, the discharging amount of the gas G3 can be adjusted. As a result, in a case where, for example, it is desired to reduce the gas abdominal pressure in the abdominal cavity 500, by operating the sheath 11 so that the taper surface 436 of the nozzle main body 43a is separated from the inner peripheral surface 118 of the sheath 11, the discharging amount of the gas G3 can be improved (increased).

In this manner, in the present embodiment, the taper surface 436 of the nozzle main body 43a and the inner peripheral surface 118 of the sheath 11 form an adjusting means for adjusting the discharging amount of the gas G3.

In the present embodiment, the nozzle head 42 is configured so that a portion in which the outer diameter changes along the longitudinal direction is omitted. In this embodiment, the outer diameter of the nozzle head 42 is constant. The outer diameter of the nozzle head 42 is smaller than the inner diameter of the sheath 11. As a result, regardless of the position of sheath 11 in the longitudinal direction of the nozzle 4, gas G3 flows in the gap 15 from the front end opening portion 113 of the sheath 11.

This embodiment omits the flange 115 on the proximal end outer peripheral portion of the sheath 11 that protrudes from the proximal end outer peripheral portion of the sheath 11 as described in the first embodiment. However, it is possible to provide such flange in this embodiment.

Figure 9:
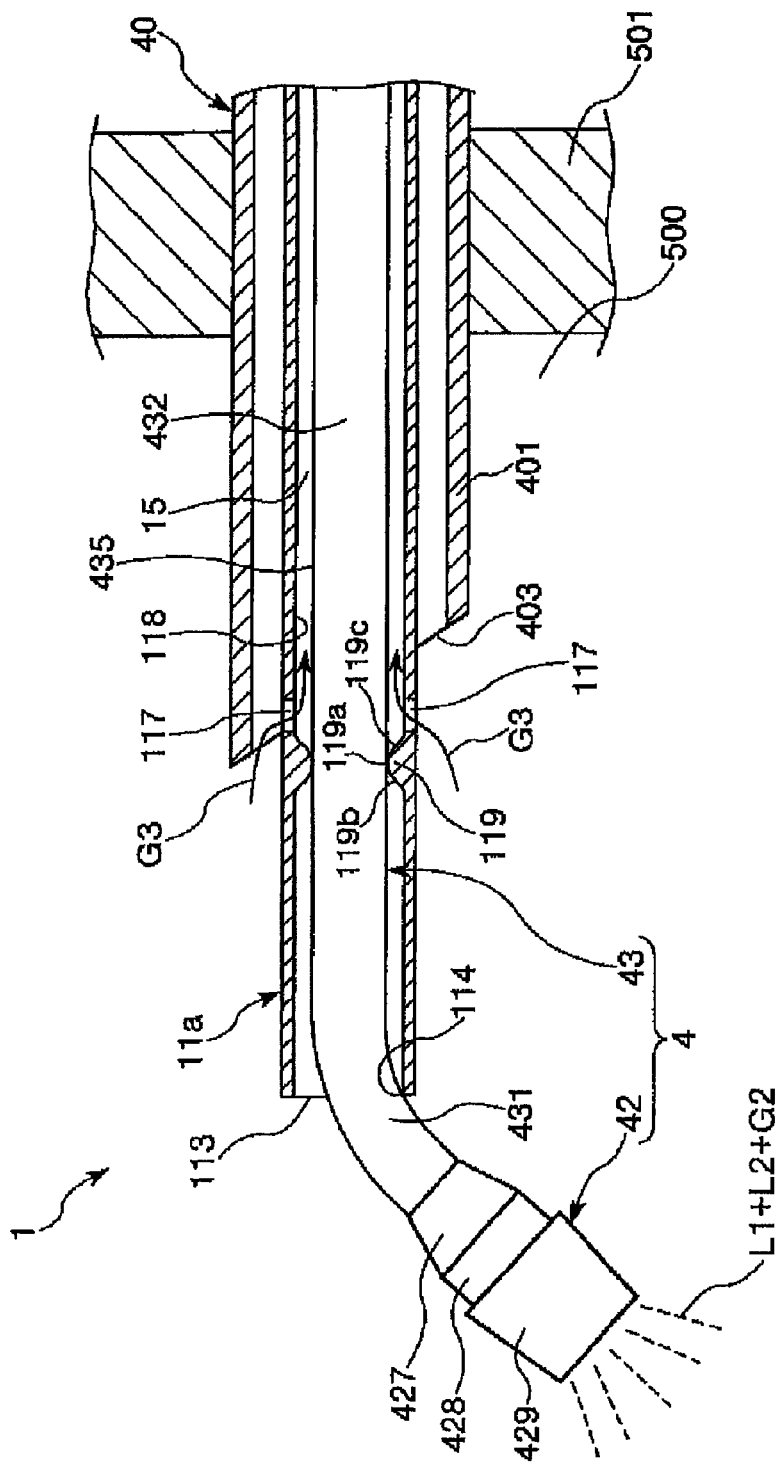
FIG. 9 is an enlarged partial longitudinal cross-sectional view of a front end side portion of an applicator according to a fourth embodiment disclosed here.

FIG. 9 illustrates the front end portion (distal end portion) of a an applicator according to a fourth embodiment disclosed here. The following description of the fourth embodiment of the applicator focuses primarily on aspects of the applicator differing from those associated with the above-described embodiments. Features associated with the fourth embodiment of the applicator that are the same as features in the embodiments described above are identified by common reference numerals and a detailed discussion of such features is not repeated.

This fourth embodiment is the same as the above-described first embodiment, except that a positioning means has a different configuration.

As shown in FIG. 9, on the inner peripheral surface 118 of a sheath 11a, a protruding portion 119 protrudes in the vicinity of the front end of the side hole 117. The protruding portion 119 is ring-shaped or annular-shaped, extending circumferentially along the inner peripheral surface 118 of the sheath 11a. As a result, in the protruding portion 119, the inner diameter of the sheath 11a is reduced. The protruding portion 119 includes a peak portion 119a in contact with the outer peripheral surface 435 of the nozzle main body 43. As a result, when the sheath 11a moves, the peak portion 119a of the protruding portion 119 slides on the outer peripheral surface 435 of the nozzle main body 43 so that frictional resistance is generated between the peak portion 119a of the protruding portion 119 and the outer peripheral surface 435 of the nozzle main body 43. When the movement of the sheath 11a stops, the positioning of the sheath 11a with respect to the longitudinal direction of the nozzle 4 is fixed or held by virtue of the engagement between the peak portion 119a of the protruding portion 119 and the outer peripheral surface 435 of the nozzle main body 43. As a result, the slope angle θ of the nozzle head 42 can be maintained, whereby the mixture can be expelled in this state. In this manner, the protruding portion 119 functions as a positioning means.

The peak portion 19a of the protruding portion 119 possesses a spherical shape. As a result, when the sheath 11a moves, it is possible to reduce the frictional resistance between the peak portion 119a of the protruding portion 119 and the outer peripheral surface 435 of the nozzle main body 43, and thus the movement operation of the sheath can relatively easily be performed.

Both surfaces 119b and 119c converging at the peak portion 119a of the protruding portion 119, i.e., the surfaces 119b and 119c on the front end (distal end) side and the proximal end side of the protruding portion 119 are respectively sloped surfaces.

FIGS. 10-13 illustrate an applicator according to a fifth embodiment disclosed here. The following description of the fifth embodiment of the applicator focuses primarily on aspects of the applicator differing from those associated with the above-described embodiments. Features in the fifth embodiment of the applicator that are the same as features in the above-described embodiments are identified by common reference numerals and a detailed description of such features is not repeated here.

The fifth embodiment of the applicator is the same as the first embodiment described above, except for differences in the shape of the nozzle and the configuration of the outer tube differ.

Figure 10:
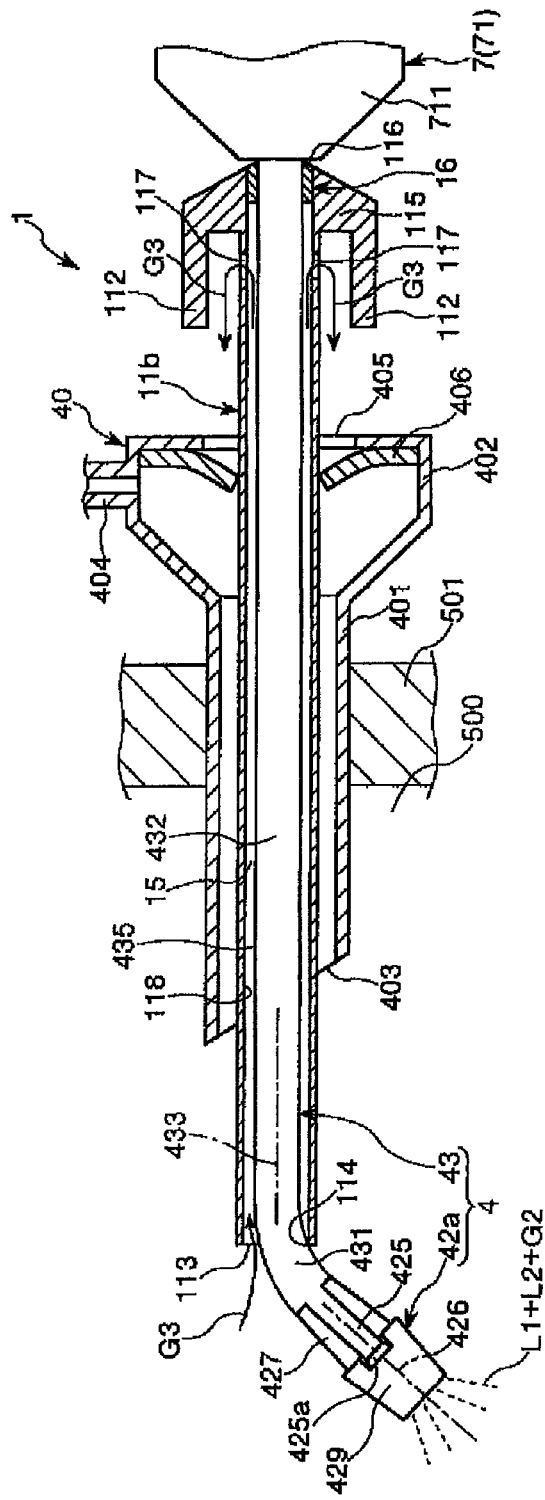
FIG. 10 is an enlarged partial longitudinal cross-sectional view of an applicator according to a fifth embodiment.
Figure 11:
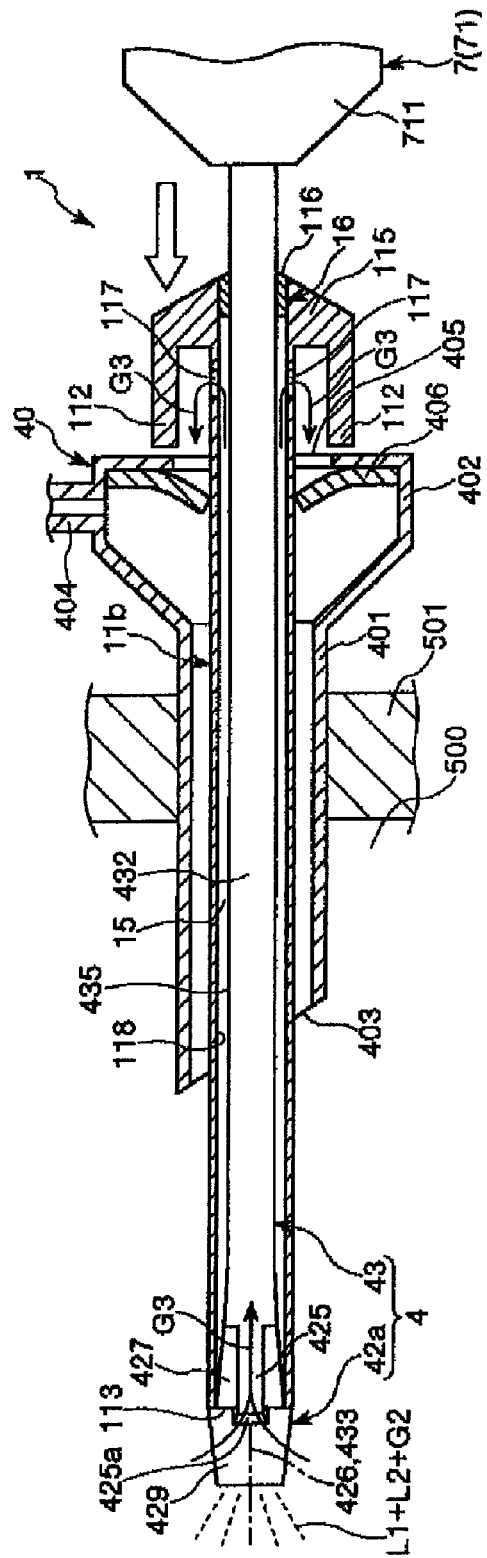
FIG. 11 is an enlarged partial longitudinal cross-sectional view of the applicator according to the fifth embodiment.
Figure 12:
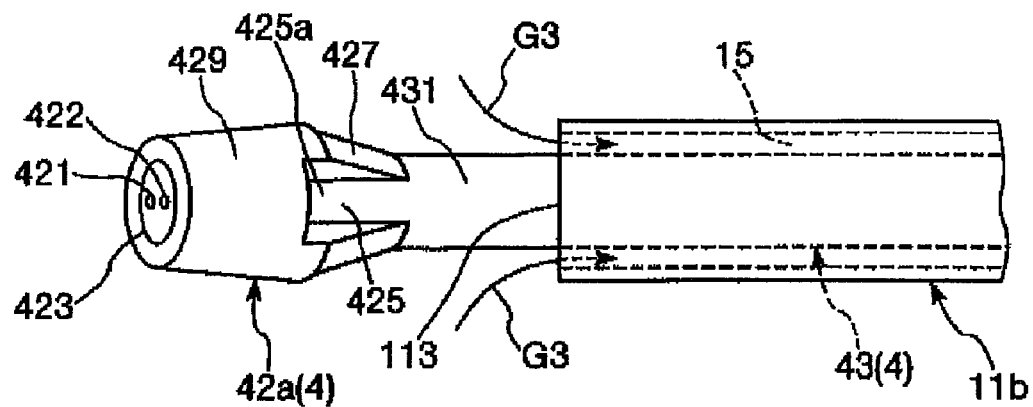
FIG. 12 is a perspective view of a front end side portion of the applicator shown in FIG. 10.
Figure 13:
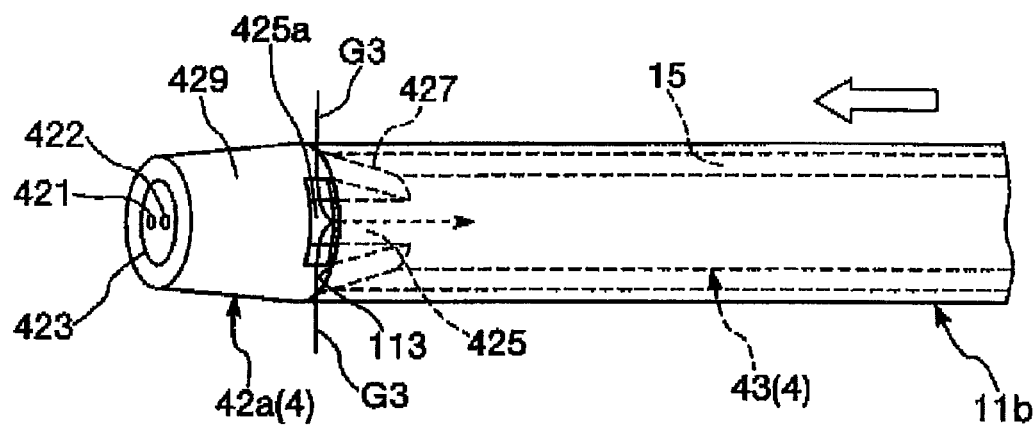
FIG. 13 is a perspective view of a front end side portion of the applicator shown in FIG. 11.

The nozzle head 42a of the nozzle 4 shown in FIGS. 10-13 does not have an outer diameter constant portion 428, and in this respect differs from the nozzle head 42 of the first embodiment. The first taper portion 427 (the fitting portion) of the nozzle head 42a includes at least one groove 425 extending along the axial direction of the nozzle head 42a. The groove 425 is configured so that the front end portion 425a of the groove extends up to the second taper portion 429. As shown in FIGS. 11 and 13, even when the axis 426 of the nozzle head 42a coincides with the axis 433 of the nozzle main body 43, the front end portion 425a of the groove 425 prevents the overall front end opening portion 113 of sheath 11b from covering nozzle head 42a (i.e., the front end opening portion 113 does not completely cover the nozzle head 42a), and sp the gap 15 communicates with the inner part of abdominal cavity 500 via the front end portion 425a of the groove 425. As a result, gas G3 within the abdominal cavity 500 can reliably flow in the gap 15 via the front end portion 425a of the groove 425.

As shown in FIGS. 10 and 11, a spacer 16 is fixed to the proximal end opening portion 116 of the sheath 11b. The spacer 16, which is fixed to the inner surface of the sheath 11b, functions in the same manner as the spacer 16 described above. For this reason, the proximal end opening portion 116 is occluded. In this case, the proximal end portion of the sheath 11b is provided with side holes 117, Specifically, the portion of the sheath 11b on the proximal end side of the trocar tube 40 with the applicator 1 inserted in the tube is provided with two side through holes 117 communicating with the gap 15. Gas G3 passing through gap 15 can reliably be discharged via the respective side holes 117. In this manner, the respective side holes 117 function as outflow ports through which the gas G passing through the gap 15 flows out.

The flange 115 of the sheath 11b includes two protruding pieces 112 protruding in the front end direction. These protruding pieces 112 are oppositely disposed (diametrically positioned) relative to the axis of the sheath 11b. When the applicator 1 is gradually pushed in the front end direction in the state in which the applicator 1 is inserted into the trocar tube 40, each protruding piece 112 of the sheath 11b respectively comes into contact with the proximal end opening portion 405 of the hub 402. As a result, the movement of the sheath 11b with respect to the trocar tube 40 in the front end direction can be restricted, and thus it is possible to inhibit or prevent the proximal end portion of the sheath 11b from carelessly entering the trocar tube 40. As a result, the proximal end portion of the sheath 11b can reliably protrude from the proximal end opening portion 405 of the trocar tube 40, thereby grasping the protruded portion. Thus, the sheath 11b can be subjected to movement operation. In this manner, each protruding piece 112 functions as the restriction means which restricts the movement limitation of the sheath 11 with respect to the trocar tube 40 in the front end direction.

Figure 14:
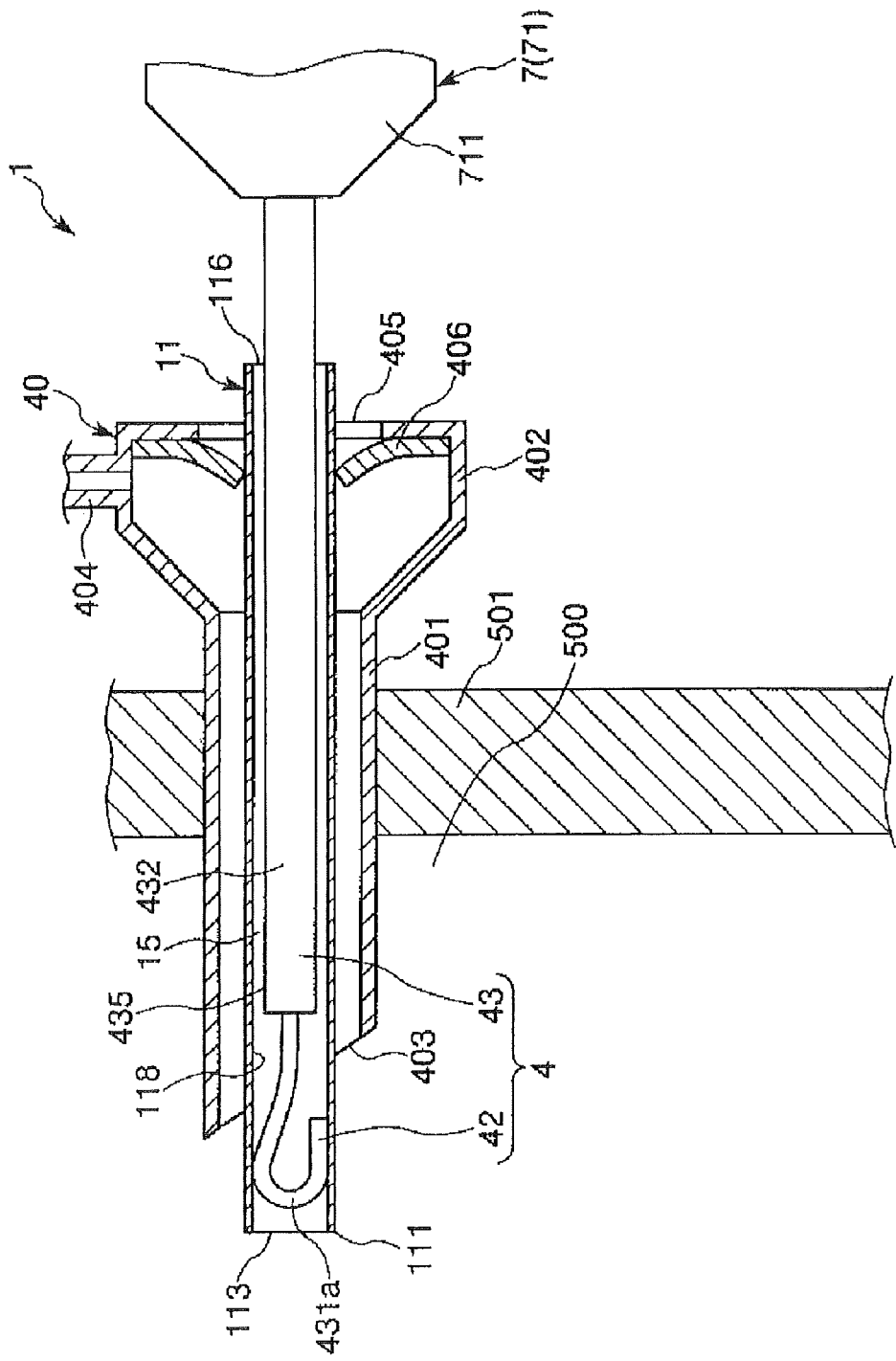
FIG. 14 is an enlarged partial longitudinal cross-sectional view of an applicator according to a sixth embodiment.
Figure 15:
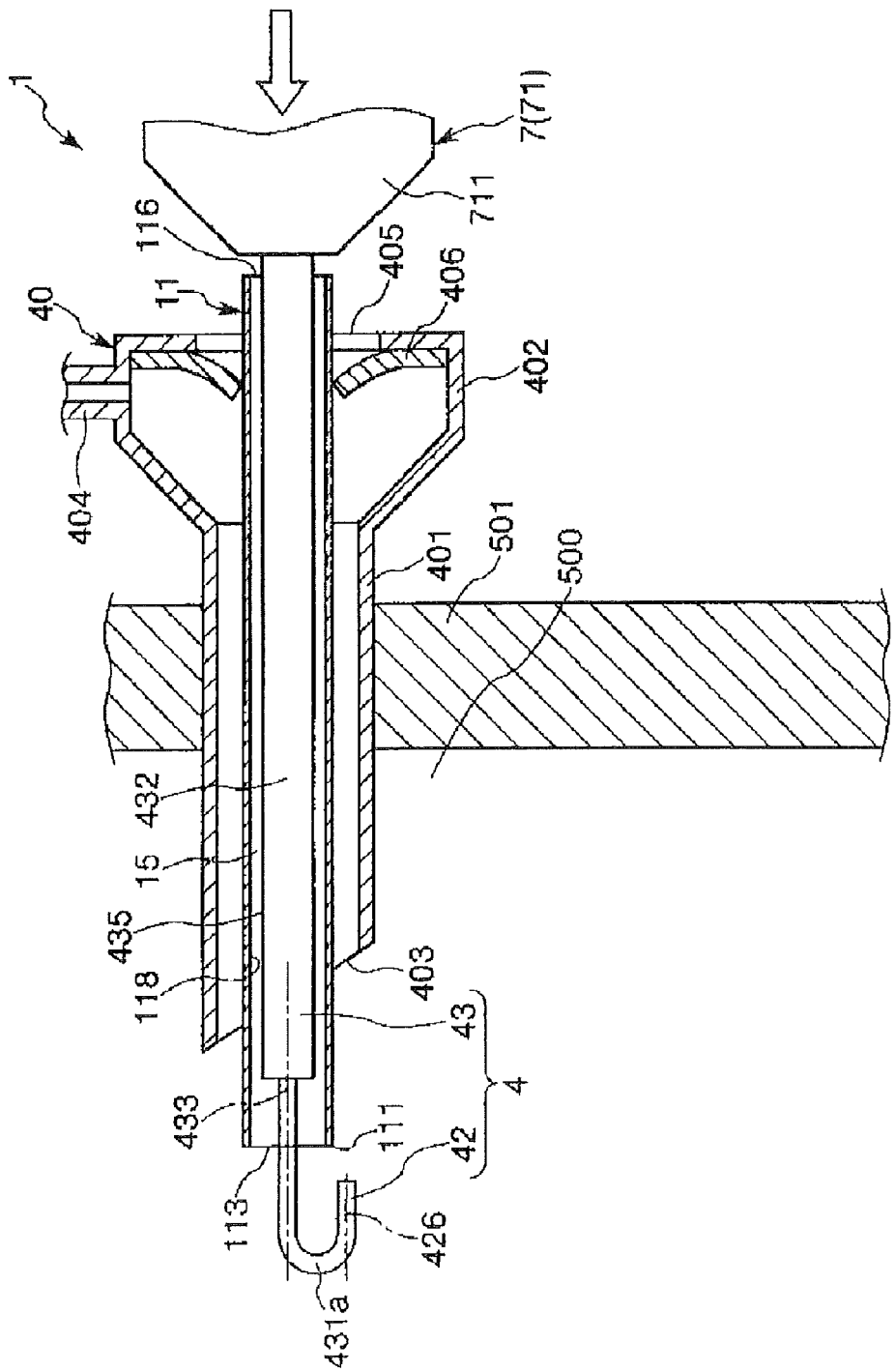
FIG. 15 is an enlarged partial longitudinal cross-sectional view of the applicator according to the sixth embodiment.

Each protruding piece 112 is respectively disposed at a position covering one of the side holes 117 of the sheath 11b from the outer peripheral side. As a result, when the proximal end portion of the sheath 11b is grasped with fingers and is subjected to movement operation, it is possible to reliably prevent each side hole 117 from being blocked by the user's fingers. Thus, the gas G3 passing through gap 15 can be reliably discharged via the side holes 117. It is to be understood that the protruding pieces 112 may nevertheless be omitted FIGS. 14 and 15 illustrate an applicator according to a sixth embodiment disclosed here. The description below of this sixth embodiment of the applicator focuses primarily on aspects of the applicator differing from those associated with the above-described embodiments. Features in the sixth embodiment of the applicator that are the same as features in the above-described embodiments are identified by common reference numerals and a detailed description of such features is not repeated here.

The present embodiment is the same as the first embodiment except that the shape of a curved section of the nozzle differs.

As shown in FIG. 15, the curved section 431a of the nozzle 4 is curved so that the curved section possesses a U-shape in its natural state (i.e., in the state in which no force is applied to the curved section). As a result, the open end of the nozzle head 42 faces toward the proximal end side in the natural state. Stated differently, the curved section results in the distal portion of the nozzle 4 being bent back upon itself. In the illustrated embodiment, the axis 426 of the nozzle head 42 is parallel to the axis 433 of the nozzle main body 43.

As shown in FIG. 14, in the state in which the entire curved section 431a is received in the sheath 11, the curved section 431a is restricted by the inner peripheral surface 118 of the sheath 11, whereby the degree of curvature of the curved section is slightly larger than in the natural state.

When the applicator main body 7 is pushed toward the front end direction from the state shown in FIG. 14, as shown in FIG. 15, the front end portion of the nozzle 4 protrudes from (i.e., distally beyond) the front end opening portion 113 of the sheath 11. At this time, the curved section 431a is in the natural state as described above, and the nozzle head 42 faces towards the rear or proximal direction.

Figure 16:
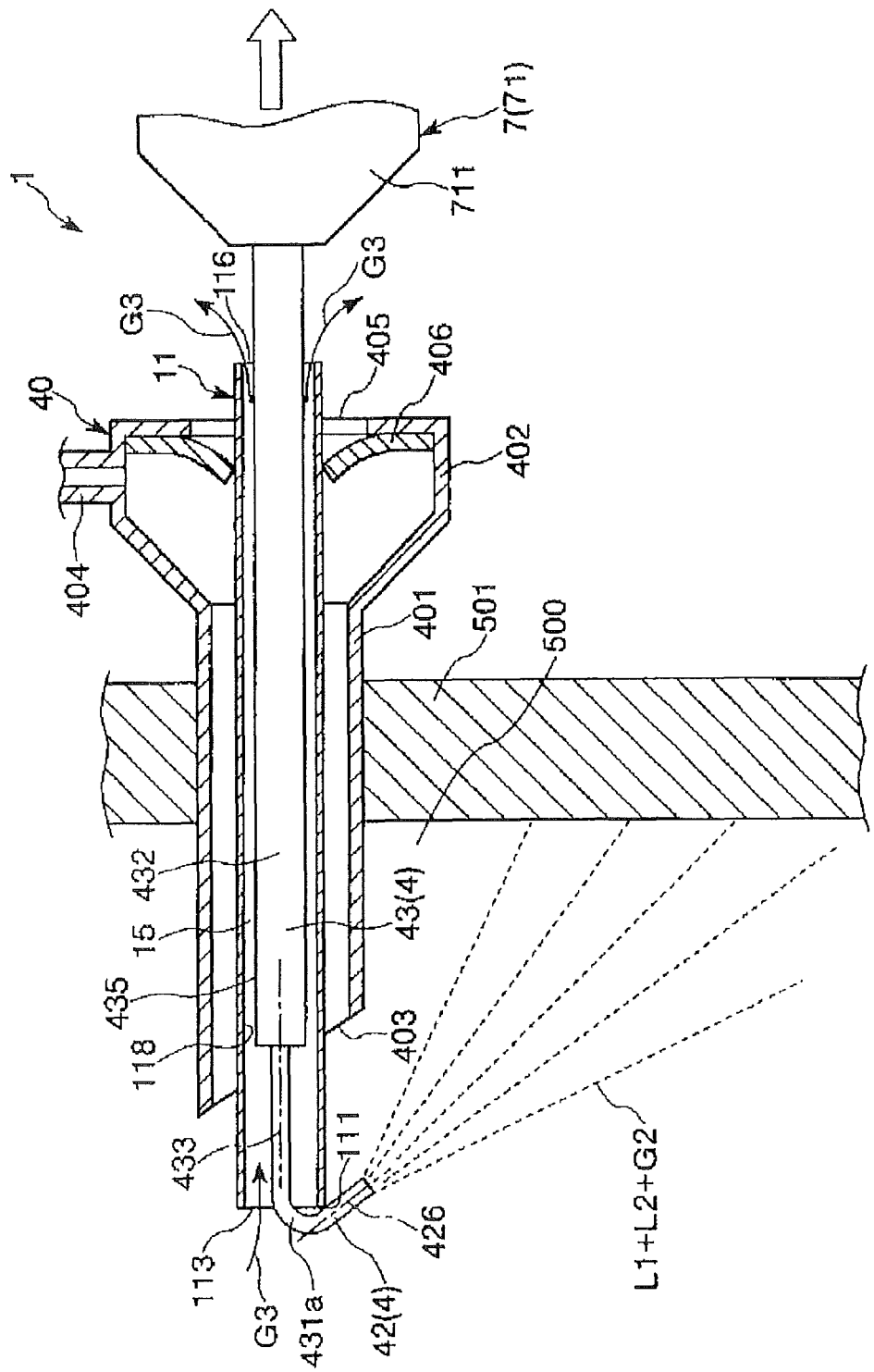
FIG. 16 is an enlarged partial longitudinal cross-sectional view of the applicator according to the sixth embodiment during use.

When applicator main body 7 is moved toward the proximal end direction from the state shown in FIG. 15, the proximal end portion of the curved section 431a is received in the sheath 11 as shown in FIG. 16, and so the nozzle head 42 (or the curved section 431a) comes into contact with the outer edge portion 111 of the front end opening portion 113 of the sheath 11. When the applicator main body 7 is further moved toward the proximal end direction, the nozzle head 42 is pressed toward the front end direction by the edge portion 111, and the shape of the curved section 431a is changed and starts to become straightened out. As a result, a degree of curvature of the curved section 431a becomes smaller than in the natural state of the curved portion, and the nozzle head 42 faces in the obliquely right and downward direction in FIG. 16. When the mixture is expelled from the nozzle head 42 in this state, the mixture is expelled toward the rear. As a result, the mixture can be applied to the portion on the rear side of the abdominal wall 501.

In a case where it is desirable to expel or direct the mixture toward the front, by further moving the applicator main body 7 from the state shown in FIG. 16 toward the proximal end direction, the curved section 431a is further straightened by the sheath 11 and is opened greater (made more straight) than the state shown in FIG. 16, whereby the nozzle head 42 faces forward. In this state, the mixture can be expelled toward the front.

The mixture may be expelled from the nozzle head 42 in the state shown in FIG. 15, that is from the state in which nozzle head 42 faces directly behind (rearward or in the proximal direction). However, in this case, the mixture may be applied to the applicator 1 as well as the rear surface of abdominal wall 501.

It is desirable that the edge portion 111 of the front end opening portion 113 of the sheath 11 be spherical.

In addition, in this embodiment, the nozzle head 42 is preferably configured to omit the portion in which the outer diameter changes along the longitudinal direction and so the outer diameter of the nozzle head 42 is constant. The outer diameter of the nozzle head 42 is smaller than the inner diameter of the sheath 11. As a result, regardless of the position of the sheath 11 in the longitudinal direction of the nozzle 4, gas G3 flows in the gap 15 from the front end portion 113 of the sheath 11 as indicated in FIG. 16.

This embodiment omits the flange 115 on the proximal end outer peripheral portion of the sheath 11 that protrudes from the proximal end outer peripheral portion of the sheath 11 as described in the first embodiment. However, it is possible to provide such flange in this embodiment.

Figure 17:
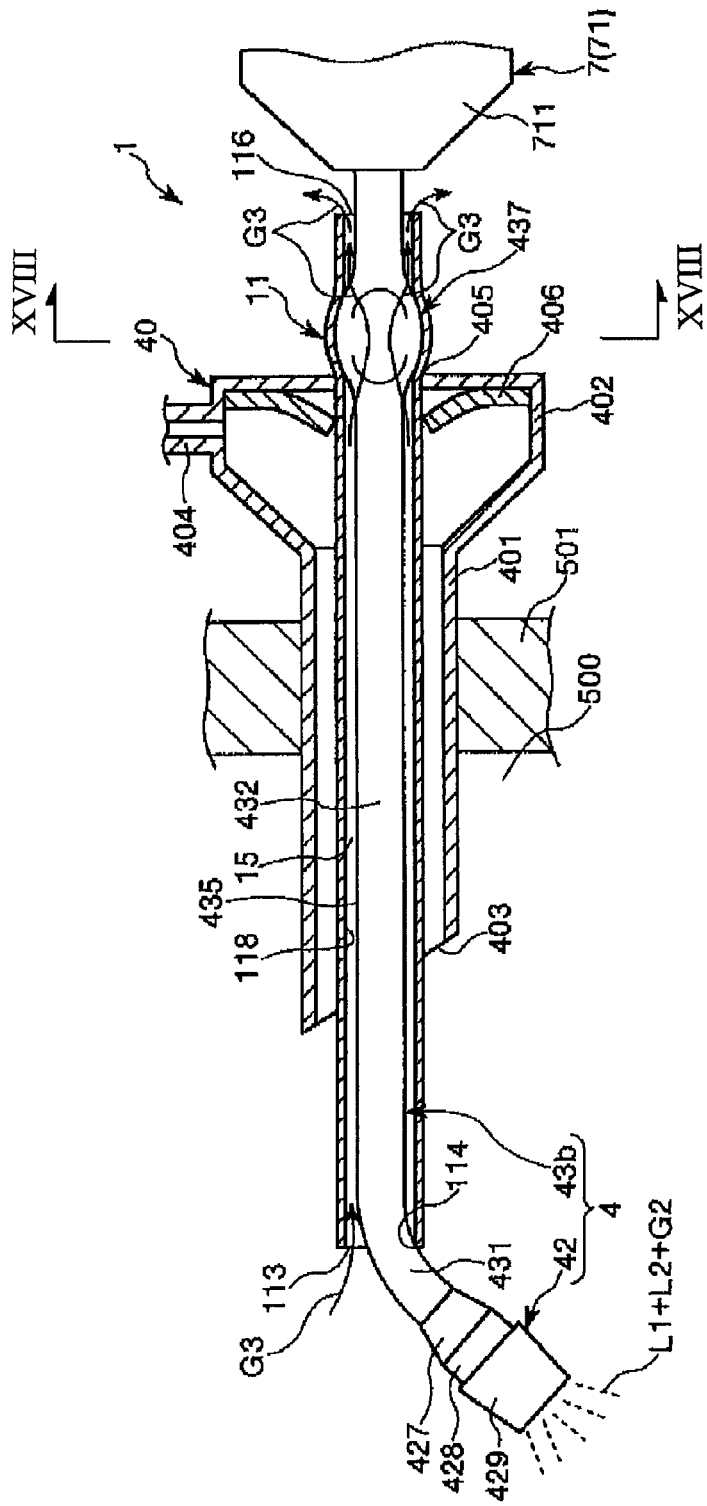
FIG. 17 is an enlarged partial longitudinal cross-sectional view of an applicator according to a seventh embodiment.
Figure 18:
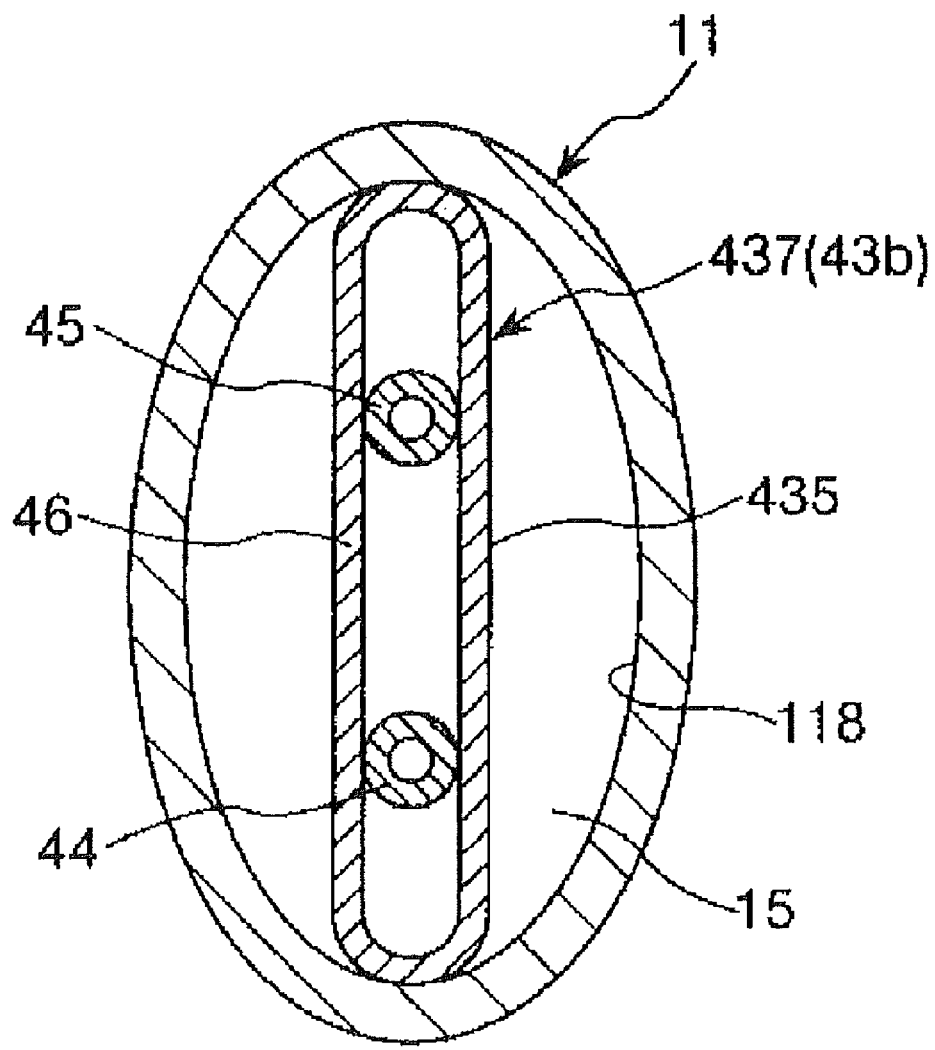
FIG. 18 is a transverse cross-sectional view of the nozzle and outer tube of the applicator taken along the section line XVIII-XVIII in FIG. 17.

FIGS. 17 and 18 illustrate a seventh embodiment of an applicator disclosed here. The following description focuses primarily on aspects of this embodiment of the applicator which differ from those associated with the above-described embodiments. Features in this seventh embodiment of the applicator that are the same as features in the above-described embodiments are identified by common reference numerals and a detailed description of such features is not repeated here.

This seventh embodiment is the same as the first embodiment, except for difference sin the partial shape of the nozzle main body of the nozzle.

As shown in FIG. 17, a flat portion 437 is formed on the proximal end portion of the nozzle main body 43b. The flat portion 437 is a portion at which the outer tube is deformed and form a third flow path 46 so as to form a flat shape as shown in FIG. 18. The length of the flat portion 437 in the vertical direction in FIG. 18 is larger than the inner diameter of the sheath 11 in the natural state. As a result, the outer peripheral surface 435 of the nozzle main body 43b in the flat portion 437 comes into close contact with the inner peripheral surface 118 of the sheath 11. When the sheath 11 moves in the longitudinal direction in this state, the inner peripheral surface 118 of the sheath 11 slides on the outer peripheral surface 435 of the flat portion 437, and frictional resistance is generated between the inner peripheral surface 118 of the sheath 11 and the outer peripheral surface 435 of the flat portion 437.

The flat portion 437 functions as a positioning means for positioning the sheath 11 relative to the longitudinal direction of the nozzle 4 in the stop position when the sheath 11 moves and stops. That is, when a force is applied to the sheath 11 to move the sheath 11 relative to the nozzle, and then the force is removed, the flat portion 437 stops relative movement of the sheath and the nozzle, and fixes the position of the sheath 11 relative to the nozzle. As a result, the slope angle θ of the nozzle head 42 can be maintained, which can expel the mixture in this state.

In addition, as mentioned above, the applicator 1 is used in the state of being inserted into the trocar tube 40. When the applicator 1 is pressed in the front end direction in this state, the outer peripheral portion of the portion where the flat portion 437 of sheath 11 is situated comes into contact with the edge portion of proximal end opening portion 405 of the hub 402 as shown in FIG. 17. As a result, the movement limitation of the sheath 11 with respect to the trocar tube 40 in the front end direction can be restricted, and so it is possible to inhibit or prevent the proximal end portion of sheath 11 from carelessly or undesirably entering the trocar tube 40, that is to inhibit or prevent the proximal end portion of the sheath 11 from moving to the front end side further than the proximal end opening portion 405 of the trocar tube 40. As a result, the proximal end portion of the sheath 11 can reliably protrude from the proximal end opening portion 405 of the trocar tube 40, thereby grasping the protruded portion. Thus, the sheath 11 can be moved and operated. In this manner, the flat portion 437 also functions as a restriction means for restricting the movement of the sheath 11 relative to trocar tube 40 in the front end direction.

While the illustrated embodiments of the applicator have been described above, the present invention is not limited to these embodiments. Parts of the applicator can be replaced with other parts capable of exhibiting the same or similar function. Components or other features can also be added.

The applicator of the present invention may be a combination of two or more configurations or aspects (characteristics) among the respective embodiments described above and illustrated in the drawing figures.

The applicator may be used by being inserted into the abdominal cavity, but is not limited in this manner. For example, the applicator may be inserted into body cavities such as a thoracic cavity and a womb.

The applicator is used in a surgery in which gas is supplied from the trocar tube into the abdominal cavity to expand the abdominal cavity, but the use of the applicator is not limited in this manner. For example, the applicator may be used in a surgery in which the abdominal wall is suspended to secure the size of the abdominal cavity, known as a suspending method.

In a case where the trocar tubes are detained in a plurality of abdominal walls in the laparoscope, among the trocar tubes, for example, the gas may be supplied from the one trocar tube, and the supply of the gas from other trocar tubes may stop.

The spacer is installed on one place over the longitudinal extent of the sheath in the first to third embodiments, but the applicator is not limited to this arrangement. Plural spacers may be installed at a plurality of spaced apart locations along the longitudinal extent of the sheath.

In the first to third embodiments, the spacer is configured so that the outer peripheral surface of the spacer is fixed to the inner peripheral surface of the sheath, and the inner peripheral surface of the spacer is movable with respect to (i.e., not fixed to) and in contact with the outer peripheral surface of the nozzle main body. However, the applicator is not limited to this arrangement. By way of example, the inner peripheral surface of the spacer may be fixed to the outer peripheral surface of the nozzle main body (so the spacer and the nozzle main body move together as a unit), and the outer peripheral surface of the spacer may be in contact with, but movable relative to (i.e., not fixed to) the inner peripheral surface of the sheath. It is to be understood that the illustration of this alternative would be similar to that shown in FIGS. 5 and 6.

The protruding portion as the positioning means is formed on the inner peripheral surface of the sheath in the fourth embodiment. However, variations on the arrangement are possible. For instance, the protruding portion may be formed on the outer peripheral surface of the nozzle main body.

Furthermore, though the applicator described above is configured to expel liquid together with the gas, it may also be used to expel powder with the gas.

The applicator disclosed here is an applicator which has useful application being inserted into the living body and includes a nozzle which has an elongated nozzle main body and a nozzle head on a front end side of the nozzle main body and through which liquid together with gas is expelled. A curved section, which is curved or bent and has flexibility, is formed on the front end portion of the nozzle main body. An outer tube through which the nozzle main body is inserted is movable along a longitudinal direction of the curved portion and an angle of a curve of the curved section changes by inserting the curved section into the outer tube, thereby adjusting the direction of the nozzle head relative to the axis of the nozzle main body. A longitudinally extending gap exists between the outer tube and the nozzle, and the gap functions as a discharge path for discharging the gas within the body cavity via the gap to the outside of the body, when a body pressure within a body cavity rises. By moving the outer tube along the longitudinal direction to suitably adjust the direction of the nozzle head relative to the axis of the nozzle main body, it is possible to expel the liquid from the nozzle head toward a plurality of places (e.g., organs, surfaces, etc.) within the body cavity, while changing the direction of the expelled liquid. Thus, the applicator can relatively easily and reliably apply liquid or powder within the body cavity over a wide range. Furthermore, due to the gas expelled from the nozzle head, the body pressure within the body cavity rises and the body cavity is expanded. When the gas continues to be expelled, the body pressure within the body cavity excessively rises, whereby the body cavity tries to further expand. However, the gas within the body cavity flows in the gap and is discharged to the outside. As a result, it is possible to suppress or prevent an excessive rise in body pressure within the body cavity, which can inhibit or prevent the body cavity from trying to expand. In addition, in cases where the curved section is curved to a degree that the nozzle head faces the proximal end side in the natural state where no external force is applied, for example when the applicator is used in laparoscopic surgery, the liquid or the powder can be applied to the rear surface (the rear portion) of the abdominal wall.

Also disclosed here is a method of applying a liquid or powder in a body cavity of a living body. The method involves positioning the distal portion of an applicator in the living body by advancing the distal portion of the applicator through a trocar in the wall of the body cavity. The applicator includes a nozzle including an elongated nozzle main body and a nozzle head at a distal end side of the nozzle main body, with the nozzle main body possessing a distal end portion that is curved or bent without application of a force to the distal end portion so that the distal end portion of the nozzle main body is configured as a curved section, and the curved section being flexible. The applicator also includes an outer tube in which is positioned at least a part of the nozzle main body, with the nozzle ahead and the curved section extending distally beyond a distal end of the outer tube. In the method, the outer tube and the nozzle are relatively moved so the curved section moves proximally relative to the outer tube and begins to enter the outer tube to adjust a direction in which the nozzle in the cavity body is facing. Gas is conveyed together with liquid or powder to the nozzle head, and the gas together with the liquid or the powder is expelled from the nozzle head toward a surface in the body cavity. This expelling of the gas and liquid/powder can also occur while the nozzle head is being adjusted.

The detailed description above describes various embodiments of the applicator. However it is to be understood that the invention is not limited to those precise embodiment and variations described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An applicator sized and configured to be inserted into a living body, the applicator comprising:
    a nozzle comprised of an elongated nozzle main body and a nozzle head through which a liquid together with a gas is expelled to deliver the liquid to a desired region in a body cavity of the living body, the nozzle head being positioned at a distal end side of the nozzle main body, the nozzle main body possessing an outer surface;
    the nozzle main body possessing a distal end portion that is curved or bent without application of a force to the distal end portion so that the distal end portion of the nozzle main body is configured as a curved section, the curved section being flexible;
    the nozzle head being distal of the curved section, the nozzle head possessing a first axis, a portion of the nozzle main body immediately proximal the curved section possessing a second axis that is not coincident with the first axis;
    an elongated outer tube having an interior open at a distal end of the outer tube and open at a proximal end of the outer tube, at least a part of the nozzle main body being positioned in the interior of the outer tube, with the curved section of the nozzle main body and the nozzle head extending distally beyond the distal end of the outer tube, the outer tube possessing an inner surface;
    the nozzle and the outer tube being relatively movable so that relative proximal movement of the outer tube with respect to the nozzle main body causes the distal end of the outer tube to contact the curved section and movably urge the curved section in a manner adjusting a direction in which the nozzle head faces;
    a longitudinally extending gap between the inner surface of the outer tube and the outer surface of the nozzle main body;
    the gap communicating with outside the outer tube and functioning as a discharge path for discharging gas within the body cavity via the gap to the outside of the living body when a body pressure within the body cavity rises;
    wherein the distal end of the outer tube is an open front end, and the nozzle head comprises a fitting portion having an outer dimension equal to an inner diameter of the open front end of the outer tube, the fitting portion being fittable into the open front end of the outer tube when the first axis of the nozzle head coincides with the second axis of the nozzle main body; and
    wherein an outer peripheral surface of the fitting portion includes at least one groove extending in an axial direction of the nozzle head, the at least one groove allowing the gas to enter into the interior of the outer tube from outside the outer tube when the fitting portion is fitted into the open front end of the outer tube.

2. The applicator according to claim 1, wherein the distal end of the outer tube is open and communicates with the gap.

3. An applicator according to claim 1, further comprising at least one elastic body either fixed to the inner surface of the outer tube and in contact with the outer surface of the nozzle main body, or fixed to the outer surface of the nozzle main body and in contact with the inner peripheral surface of the outer tube.

4. An applicator according to claim 3, wherein the outer tube includes at least one side hole passing through a wall of the outer tube to communicate the interior of the outer tube with outside the outer tube, the side hole being positioned proximally of the elastic body.

5. An applicator according to claim 1, further comprising a protruding portion which forms a part of and extends from one of the inner surface of the outer tube and the outer surface of the nozzle main body, the protruding portion possessing a peak portion in contact with the other one of the outer surface of the nozzle main body and the inner surface of the outer tube.

6. An applicator according to claim 1, wherein the nozzle head also comprises a tapering diameter portion distal of the fitting portion, the tapering diameter portion possessing an outer diameter greater than the outer dimension of the fitting portion.

7. An applicator according to claim 1, wherein the nozzle main body comprises two separated flow paths each extending from a fluid source to the nozzle head, and the nozzle main body also comprises a gas flow path extending from a gas supply to the nozzle head.

8. An applicator sized and configured to be inserted into a living body, the applicator comprising:
   a nozzle comprised of an elongated nozzle main body and a nozzle head through which a liquid together with a gas is expelled to deliver the liquid to a desired region in a body cavity of the living body, the nozzle head being positioned at a distal end side of the nozzle main body;
   the nozzle main body possessing a distal end portion that is curved or bent without application of a force to the distal end portion so that the distal end portion of the nozzle main body is configured as a curved section, the curved section being flexible;
   an outer tube possessing a distal end and having a hollow interior sized to permit at least a portion of the nozzle main body to be positioned in the hollow interior of the outer tube, the outer tube and the nozzle main body being relatively movable so that the outer tube relatively moves along a longitudinal extent of the nozzle main body;
   relative movement of the outer tube and the nozzle main body in a manner causing the proximal relative movement of the nozzle main body with respect to the outer tube, while a portion of the nozzle main body is in the hollow interior of the outer tube and the curved section extends distally beyond the distal end of the outer tube, causing a configuration of the curved section to change and start to become more straightened to thereby adjust a direction of the nozzle head relative to an axis of the nozzle main body;
   the outer tube possessing an inner diameter larger than an outer diameter of the nozzle main body so that with the nozzle main body positioned in the outer tube, a longitudinally extending gap exists between an inner peripheral surface of the outer tube and an outer peripheral surface of the nozzle main body, the gap functioning as a discharge path for discharging gas within the body cavity via the gap to outside the living body when a body pressure within the body cavity rises;
   wherein the distal end of the outer tube is an open front end, and the nozzle head comprises a fitting portion having an outer dimension equal to an inner diameter of the open front end of the outer tube, the fitting portion being fittable into the open front end of the outer tube when an axis of the nozzle head coincides with an axis of the nozzle main body; and
   wherein an outer peripheral surface of the fitting portion includes at least one groove extending in an axial direction of the nozzle head, the at least one groove allowing the gas to enter into the hollow interior of the outer tube from outside the outer tube when the fitting portion is fitted into the open front end of the outer tube.

9. The applicator according to cliam 8, further comprising positioning means for positioning the outer tube with respect to the longitudinal extent of the nozzle main body.

10. An applicator according to claim 9, wherein the positioning means includes at least one elastic body either fixed to the inner peripheral surface of the outer tube and in contact with the outer peripheral surface of the nozzle main body, or fixed to the outer peripheral surface of the nozzle main body and in contact with the inner peripheral surface of the outer tube.

11. An applicator according to claim 10, wherein the outer tube includes at least one side hole passing through a wall of the outer tube to communicate the interior of the outer tube with outside the outer tube, the side hole being positioned proximally of the elastic body.

12. An applicator according to claim 9, wherein the positioning means includes a protruding portion which forms a part of and extends from one of the inner peripheral surface of the outer tube and the outer peripheral surface of the nozzle main body, the protruding portion possessing a peak portion in contact with the other one of the outer peripheral surface of the nozzle main body and the inner peripheral surface of the outer tube.

13. An applicator according to claim 8, wherein the nozzle main body comprises two separated flow paths each extending from a different fluid source to the nozzle head, and the nozzle main body also comprises a gas flow path extending from a gas supply to the nozzle head.

* * * * *